United States Patent
Dehesh et al.

(10) Patent No.: US 6,489,461 B1
(45) Date of Patent: Dec. 3, 2002

(54) NUCLEIC ACID SEQUENCES ENCODING PROTEINS INVOLVED IN FATTY ACID BETA-OXIDATION AND METHODS OF USE

(75) Inventors: Katayoon Dehesh, Vacaville; Byron Froman, Davis, both of CA (US)

(73) Assignee: Calgene LLC, Davis, CA (US)

( * ) Notice: Subject to any disclaimer, the term of this patent is extended or adjusted under 35 U.S.C. 154(b) by 50 days.

(21) Appl. No.: 09/591,095

(22) Filed: Jun. 8, 2000

Related U.S. Application Data

(60) Provisional application No. 60/138,162, filed on Jun. 8, 1999.

(51) Int. Cl.[7] .................. C07H 21/04; A01H 11/00; A01H 5/00; C12N 5/04; C12N 15/82; C12N 15/74

(52) U.S. Cl. .................. 536/23.6; 536/23.1; 800/295; 800/298; 435/419; 435/468; 435/471

(58) Field of Search .................. 800/295, 298; 536/23.1, 23.6; 435/468, 419, 471

(56) References Cited

FOREIGN PATENT DOCUMENTS

| EP | 0 894 864 A1 | 2/1999 | ............ C12N/15/82 |
|----|----|----|----|
| WO | WO 97/43422 | 11/1997 | ............ C12N/15/53 |
| WO | WO 97/44465 | 11/1997 | ............ C12N/15/53 |
| WO | WO 99/45122 | 9/1999 | ............ C12N/15/52 |

OTHER PUBLICATIONS

Schafer et al, "An example of intron junctional sliding in the gene families encoding squalene monooxygenase homologues in *Arabidopsis thaliana* and *Brassica napus* ", 1999, Plant Molecular Biology, pp. 721–728.*
Bork et al.,"Go hunting in sequence databases but watch our for the traps", Oct. 1996, TIG vol. 12 No. 10, pp. 425–427.*
Smith et al., The challenges of genome sequence annotation or "The Devil is in the details", Nov. 1997, Nature Biotechnology vol. 15, pp. 1222–1223.*
Doerks,"Protein annotation: detective work for function prediction", Jun. 1998, vol. 14, No. 6, pp. 248–250.*
Brenner, "Errors in genome annotation", Apr. 1999, vol. 15 No. 4.*
Froman et al, "ACX3, a Novel Medium–Chain Acyl–Coenzyme A Oxidase from Arabidopsis", Jun. 2000, Plant Physiology vol. 123, pp. 733–741.*
Eastmond et al, "Promoter Trapping of a Novel Medium–chain Acyl–CoA Oxidase, which is iniduced Transcriptionally during Arabidopsis Seed Germination", 2000, The Journal of Biological Chemistry vol. 275, pp. 34375–34381.*

Accession No. AF057044, XP002157738: "An acyl–CoA oxidase gene of *Arabidopsis thaliana*, " Apr. 15, 1998.
Accession No. 065202, XP002157739: "Acyl–CoA Oxidase (EC 1.3.3.6)" Aug. 1998.
Accession No. Z97341, XP002157740: "*Arabidopsis thaliana* DNA chromosome 4, ESSA I FCA contig fragment No. 6, " Jul. 4, 1997.
Accession No. 023518, XP002157741: "Analysis of 1.9 Mb of contiguous sequence from chromosome 4 of *Arabidopsis thaliana*," Jan. 1, 1998.
Accession No. AC006068, XP002157741: "Sequence and analysis of chromosome 2 of the plant *Arabidopsis thaliana*," Nov. 27, 1998.
Accession No. Q9ZQP2, XP0022157743: "*Arabidopsis thaliana* chromosome II BAC T20F21 genomic sequence," May 1, 1999.
Eccleston, Victoria S., et al. "Expression of Lauroyl–Acyl Carrier Protein Thioesterase in *Brassica napus* Seeds Induces Pathways for Both Fatty Acid Oxidation and Biosynthesis and Implies a Set Point for Triacylglycerol Accumulation," The Plant Cell 10: 613–621 (1998).
Hayashi, Hiroshi, et al. "A Novel Acyl–CoA Oxidase That Can Oxidize Short–chain Acyl–CoA in Plant Peroxisomes," The Journal of Biological Chemistry 274(18): 12715–12721 (1999).
Hooks, Mark A., et al. "Long–chain acyl–CoA oxidases of Arabidopsis" The Plant Journal 20(1): 1–13 (1999).
Hooks, Mark A., et al. "An antisense approach to study beta–oxidation," Journal of Experimental Botany 49: 56 May supplement (1998).
Olesen, Christian, et al. "The glyoxysomal 3–ketoacyl–CoA thiolase precursor from *Brassica napus* has enzymatic activity when synthesized in *Escherichia coli*," FEBS Letters 412: 138–140 (1997).
International Search Report PCT/US 00/16149, Entitled: Nucleic Acid Sequences EnCoding Proteins Involved in Fatty Acids Beta–Oxidation and Methods of Use, Applicant: Calgene LLC, Jun. 8, 2000.

* cited by examiner

*Primary Examiner*—Elizabeth F. McElwain
*Assistant Examiner*—Stuart Baum
(74) *Attorney, Agent, or Firm*—Arnold & Porter; Brian K. Stierwalt

(57) ABSTRACT

The invention provides novel polynucleotide and polypeptide sequences involved in fatty acid beta-oxidation and to methods of producing such polypeptides using recombinannt techniques. In addition, methods are provided for using such sequences to alter lipid levels in plants by altering fatty acid beat-oxidation in host plant cells.

9 Claims, 1 Drawing Sheet

ACOX Activity (mU/mg)

A. Developing Seeds

B. Germinating Seeds

SEQUENCE LISTING

<160> NUMBER OF SEQ ID NOS: 27

<210> SEQ ID NO 1
<211> LENGTH: 2300
<212> TYPE: DNA
<213> ORGANISM: Arabidopsis sp.

<400> SEQUENCE: 1

```
tttttttcct atcatctctg agagttttct cgagaaactt ttgagtgttt agctactaga       60
ttctgaatta cgaatcatgg aaggaattga tcacctcgcc gatgagagaa acaaagcaga      120
gttcgacgtt gaggatatga agatcgtctg ggctggttcc cgccacgctt ttgaggtttc      180
cgatcgaatt gcccgccttg tcgccagcga tccggtgttt gagaaaagca atcgagctcg      240
gttgagtagg aaggagctgt ttaagagtac gttgagaaaa tgtgcccatg cgtttaaaag      300
gattatcgag cttcgtctca atgaggaaga agcaggaaga ttgaggcact ttatcgacca      360
gcctgcctat gtggatctgc actggggaat gtttgtgcct gctattaagg ggcagggtac      420
agaggagcag cagaagaagt ggttgtcgct ggccaataag atgcagatta ttgggtgtta      480
tgcacagact gagcttggtc atggctcaaa tgttcaagga cttgagacaa ctgccacatt      540
tgatcccaag actgatgagt ttgtaattca cactccaact cagactgcat ccaaatggtg      600
gcctggtggt ttgggaaaag tttctactca tgctgttgtt tacgctcgtc tcataactaa      660
cggaaaagac tacggtatcc atggattcat cgtgcaactg cgaagcttag aagatcattc      720
tcctcttccg aatataactg ttggtgatat cgggacaaag atgggaaatg gagcatataa      780
ttcaatggac aacgggtttc ttatgtttga tcatgttcgc attcctagag atcaaatgct      840
catgaggctg tcaaaagtta caagagaagg agaatatgtt ccatcggatg ttccaaagca      900
gctggtatat ggtactatgg tgtatgtgag acaaacaatt gtggctgatg cttccaatgc      960
actatctcga gcagtttgca tagctacaag atacagtgca gtgcggaggc aatttggcgc     1020
acataatggt ggcattgaga cacaggtgat tgattataaa actcagcaga acaggctatt     1080
tcctctgcta gcatctgcat atgcatttcg atttgttgga gagtggctaa aatggctgta     1140
cacggatgta actgaaagac tggcggctag tgatttcgca actttgcctg aggctcatgc     1200
atgcactgca ggattgaagt ctctcaccac cacagccact gcggatggca ttgaagaatg     1260
tcgtaagtta tgtggtggac atggatactt gtggtgcagt gggctccccg agctgtttgc     1320
tgtatatgtt cctgcctgca catacgaagg agacaatgtt gtgctgcaat tacaggttgc     1380
tcgattcctc atgaagacag tcgcccagct gggatctgga aaggttcctg ttggcacaac     1440
tgcttatatg ggccgggcag cacatctttt gcaatgtcgt tctggtgttc aaaaggctga     1500
```

-continued

```
ggattggtta aaccctgatg ttgtactgga agctttcgaa gctagggctc tcagaatggc    1560
tgttacgtgt gccaaaaatc tcagcaagtt tgagaatcag gaacaaggat ccaagagct    1620 cttggctgat tggttgagg ccgctattgc tcattgccaa ttgattgttg tttccaagtt    1680
catagcgaaa ctggagcaag acataggtgg caaaggagtg aagaaacagc tgaataatct    1740
gtgttacatt tatgctcttt atctcctcca caaacatctc ggcgatttcc tctccactaa    1800
ctgcatcact cccaaacaag cctctcttgc taacgaccag ctccgttcct tatacactca    1860
ggtccggcct aatgcggttg cacttgtgga cgccttcaat tacaccgacc attacttgaa    1920
ctcggttctt ggccgttacg acggtaatgt gtacccaaag ctctttgagg aagcgttgaa    1980
ggatccattg aacgactcgg tggttcctga tgggtaccaa gaataccttc gacctgtgct    2040
tcagcagcaa cttcgtaccg ctaggctctg aagagttttc tttgcttgat actcgatatg    2100
gttaatcaca ttagacttgc ttcgtccttc ttcttcgtct tcttcttctt ctcgctttga    2160
ataatttcgc agtttaaaaa ctggcgatgc ccttatttat atgtagcaat gtaatagtta    2220
atgtacgatc gtcatatggc ggaattttag tactattttt cgttttcaat gcaacattaa    2280
tacaattgat cgtttctact                                                2300
```

<210> SEQ ID NO 2
<211> LENGTH: 664
<212> TYPE: PRT
<213> ORGANISM: Arabidopsis sp.

<400> SEQUENCE: 2

```
Met Glu Gly Ile Asp His Leu Ala Asp Glu Arg Asn Lys Ala Glu Phe
 1               5                  10                  15

Asp Val Glu Asp Met Lys Ile Val Trp Ala Gly Ser Arg His Ala Phe
            20                  25                  30

Glu Val Ser Asp Arg Ile Ala Arg Leu Val Ala Ser Asp Pro Val Phe
        35                  40                  45

Glu Lys Ser Asn Arg Ala Arg Leu Ser Arg Lys Glu Leu Phe Lys Ser
    50                  55                  60

Thr Leu Arg Lys Cys Ala His Ala Phe Lys Arg Ile Ile Glu Leu Arg
65                  70                  75                  80

Leu Asn Glu Glu Glu Ala Gly Arg Leu Arg His Phe Ile Asp Gln Pro
                85                  90                  95

Ala Tyr Val Asp Leu His Trp Gly Met Phe Val Pro Ala Ile Lys Gly
            100                 105                 110

Gln Gly Thr Glu Glu Gln Gln Lys Lys Trp Leu Ser Leu Ala Asn Lys
        115                 120                 125

Met Gln Ile Ile Gly Cys Tyr Ala Gln Thr Glu Leu Gly His Gly Ser
    130                 135                 140

Asn Val Gln Gly Leu Glu Thr Thr Ala Thr Phe Asp Pro Lys Thr Asp
145                 150                 155                 160

Glu Phe Val Ile His Thr Pro Thr Gln Thr Ala Ser Lys Trp Trp Pro
                165                 170                 175

Gly Gly Leu Gly Lys Val Ser Thr His Ala Val Val Tyr Ala Arg Leu
            180                 185                 190

Ile Thr Asn Gly Lys Asp Tyr Gly Ile His Gly Phe Ile Val Gln Leu
        195                 200                 205

Arg Ser Leu Glu Asp His Ser Pro Leu Pro Asn Ile Thr Val Gly Asp
    210                 215                 220

Ile Gly Thr Lys Met Gly Asn Gly Ala Tyr Asn Ser Met Asp Asn Gly
```

```
225                 230                 235                 240
Phe Leu Met Phe Asp His Val Arg Ile Pro Arg Asp Gln Met Leu Met
                245                 250                 255
Arg Leu Ser Lys Val Thr Arg Glu Gly Glu Tyr Val Pro Ser Asp Val
                260                 265                 270
Pro Lys Gln Leu Val Tyr Gly Thr Met Val Tyr Val Arg Gln Thr Ile
                275                 280                 285
Val Ala Asp Ala Ser Asn Ala Leu Ser Arg Ala Val Cys Ile Ala Thr
                290                 295                 300
Arg Tyr Ser Ala Val Arg Arg Gln Phe Gly Ala His Asn Gly Gly Ile
305                 310                 315                 320
Glu Thr Gln Val Ile Asp Tyr Lys Thr Gln Gln Asn Arg Leu Phe Pro
                325                 330                 335
Leu Leu Ala Ser Ala Tyr Ala Phe Arg Phe Val Gly Glu Trp Leu Lys
                340                 345                 350
Trp Leu Tyr Thr Asp Val Thr Glu Arg Leu Ala Ala Ser Asp Phe Ala
                355                 360                 365
Thr Leu Pro Glu Ala His Ala Cys Thr Ala Gly Leu Lys Ser Leu Thr
                370                 375                 380
Thr Thr Ala Thr Ala Asp Gly Ile Glu Glu Cys Arg Lys Leu Cys Gly
385                 390                 395                 400
Gly His Gly Tyr Leu Trp Cys Ser Gly Leu Pro Glu Leu Phe Ala Val
                405                 410                 415
Tyr Val Pro Ala Cys Thr Tyr Glu Gly Asp Asn Val Val Leu Gln Leu
                420                 425                 430
Gln Val Ala Arg Phe Leu Met Lys Thr Val Ala Gln Leu Gly Ser Gly
                435                 440                 445
Lys Val Pro Val Gly Thr Thr Ala Tyr Met Gly Arg Ala Ala His Leu
450                 455                 460
Leu Gln Cys Arg Ser Gly Val Gln Lys Ala Glu Asp Trp Leu Asn Pro
465                 470                 475                 480
Asp Val Val Leu Glu Ala Phe Glu Ala Arg Ala Leu Arg Met Ala Val
                485                 490                 495
Thr Cys Ala Lys Asn Leu Ser Lys Phe Glu Asn Gln Glu Gln Gly Phe
                500                 505                 510
Gln Glu Leu Leu Ala Asp Leu Val Glu Ala Ile Ala His Cys Gln
                515                 520                 525
Leu Ile Val Val Ser Lys Phe Ile Ala Lys Leu Glu Gln Asp Ile Gly
                530                 535                 540
Gly Lys Gly Val Lys Lys Gln Leu Asn Leu Cys Tyr Ile Tyr Ala
545                 550                 555                 560
Leu Tyr Leu Leu His Lys His Leu Gly Asp Phe Leu Ser Thr Asn Cys
                565                 570                 575
Ile Thr Pro Lys Gln Ala Ser Leu Ala Asn Asp Gln Leu Arg Ser Leu
                580                 585                 590
Tyr Thr Gln Val Arg Pro Asn Ala Val Ala Leu Val Asp Ala Phe Asn
                595                 600                 605
Tyr Thr Asp His Tyr Leu Asn Ser Val Leu Gly Arg Tyr Asp Gly Asn
                610                 615                 620
Val Tyr Pro Lys Leu Phe Glu Glu Ala Leu Lys Asp Pro Leu Asn Asp
625                 630                 635                 640
Ser Val Val Pro Asp Gly Tyr Gln Glu Tyr Leu Arg Pro Val Leu Gln
                645                 650                 655
```

Gln Gln Leu Arg Thr Ala Arg Leu
        660

<210> SEQ ID NO 3
<211> LENGTH: 1992
<212> TYPE: DNA
<213> ORGANISM: Arabidopsis sp.

<400> SEQUENCE: 3

| | | | | | |
|---|---|---|---|---|---|
| atggagagag | ttgatcacct | tgctgatgag | aggaacaaag | cagagttcaa | cgtcgacgat | 60 |
| atgaagatcg | tctgggccgg | ttcccgccac | gctttcgatg | tttcaaatcg | tatgtctcgc | 120 |
| ctcgtcgcta | atgatctggt | ctttgagaaa | agcaaaagag | ctgtgatgag | taggaaagag | 180 |
| ttgttcaaga | acacgttgag | gaaaagtgtt | cacgcttgga | agttgattaa | cgagcttcgt | 240 |
| ctctcagatg | aggaaggact | caaattgaga | tctttcatgg | atcaaccagg | cttcttggat | 300 |
| ctgcattggg | gaatgtttgt | gcctgcaatt | aaaggacaag | gcacagagga | acaacaacaa | 360 |
| aagtggttgt | ctttagctac | taagatgcag | ataattggat | gttatgctca | aactgagctt | 420 |
| ggtcatggct | ctaatgttca | aggccttgag | acaaccgcta | cttttgatcc | aaagacagat | 480 |
| cagtttatca | ttcacagtcc | aactcagaca | tcatccaaat | ggtggcctgg | tgggttagga | 540 |
| aaagtttcta | ctcatgctgt | tatttatgct | cgtctaataa | ccaatggcaa | agaccatggt | 600 |
| gtacatggat | tcatcgtgca | gctgcgtagt | ttggatgatc | attctcctct | tccgggtata | 660 |
| accgttggtg | atatcggaat | gaagtttgga | acgggcat | ataactcaat | ggacaatggt | 720 |
| tttcttatgt | ttgatcattt | tcgcattcct | agagatcaaa | tgctcatgag | actgttaaaa | 780 |
| gttacaagag | aaggaaaata | tgtagcatca | gatgttccaa | ggcaattggt | gtatggtact | 840 |
| atggtgtatg | tgagacagtc | tattgtgtca | aatgcttcca | ccgcgctggc | tcgggcagtt | 900 |
| tgcattgcta | ctaggtacag | tgctgttcga | aggcagtttg | gctcacatga | tggtggcatt | 960 |
| gagacacagg | tgattgatta | taaaactcag | cagaacaggt | tgtttcctct | gctggcatct | 1020 |
| gcatatgcat | ttcggtttgt | aggggaatgg | ctgaagtggc | tctacactga | tgtaacaaaa | 1080 |
| agactagagg | ccagtgattt | cgcaacattg | cctgaagctc | atgcatgcac | tgctggattg | 1140 |
| aagtctatga | ctacctcagc | cacctctgat | gggattgaag | aatgtcgtaa | gttatgtggt | 1200 |
| ggacatggat | acttgtggtg | tagtgggctt | cctgaattgt | ttgctgtata | tgttcctgct | 1260 |
| tgcacatacg | agggagacaa | tgttgtgttg | cagttacagg | ttgctagatt | tctgatgaag | 1320 |
| acagtttcac | agttgggttc | tggaaaggct | ccttctggga | caactgctta | tatgggcaga | 1380 |
| gcaaaacacc | ttttgcaatg | cagttccgga | gttcgaaatg | ctagggactg | gttaaacccc | 1440 |
| ggtatggtgt | tggaatcttt | tgaagcaaga | gctttgagaa | tggctgttac | tcgtgctaac | 1500 |
| aatctaagca | agtttgagaa | tcaagaacaa | ggattctcag | aactcttggc | tgatcctgtt | 1560 |
| gaggctgcta | ctgctcattg | ccagttaatt | gttgtttcta | agtttatagc | caaagtagag | 1620 |
| ggagatattg | aaggaaaagg | agtgaagaaa | cagctcaaga | atctatgcta | catgtacgca | 1680 |
| ctctatctcc | ttcacaaaca | ccttggtgat | ttcctcagta | caaactctgt | tactcctgaa | 1740 |
| caagcctcac | ttgcgaacca | gcagcttcga | tcactctact | ctcaggttcg | accaaacgca | 1800 |
| gtggccctag | tggacgcctt | cgactacacg | gaccagtatc | ttggctctgt | cttaggccgc | 1860 |
| tatgacggaa | acgtttatcc | aaagcttttc | gaggaagcgt | tgaaggatcc | actcaatgac | 1920 |
| tcggtggttc | ctgacggcta | ccgtgagtac | atccgaccgt | tgattaagca | acgcttccgc | 1980 |
| tctgccaaac | tc | | | | | 1992 |

```
<210> SEQ ID NO 4
<211> LENGTH: 664
<212> TYPE: PRT
<213> ORGANISM: Arabidopsis sp.

<400> SEQUENCE: 4

Met Glu Arg Val Asp His Leu Ala Asp Glu Arg Asn Lys Ala Glu Phe
 1               5                  10                  15

Asn Val Asp Asp Met Lys Ile Val Trp Ala Gly Ser Arg His Ala Phe
            20                  25                  30

Asp Val Ser Asn Arg Met Ser Arg Leu Val Ala Asn Asp Leu Val Phe
        35                  40                  45

Glu Lys Ser Lys Arg Ala Val Met Ser Arg Lys Glu Leu Phe Lys Asn
 50                  55                  60

Thr Leu Arg Lys Ser Val His Ala Trp Lys Leu Ile Asn Glu Leu Arg
 65                  70                  75                  80

Leu Ser Asp Glu Glu Gly Leu Lys Leu Arg Ser Phe Met Asp Gln Pro
                85                  90                  95

Gly Phe Leu Asp Leu His Trp Gly Met Phe Val Pro Ala Ile Lys Gly
            100                 105                 110

Gln Gly Thr Glu Glu Gln Gln Lys Trp Leu Ser Leu Ala Thr Lys
        115                 120                 125

Met Gln Ile Ile Gly Cys Tyr Ala Gln Thr Glu Leu Gly His Gly Ser
130                 135                 140

Asn Val Gln Gly Leu Glu Thr Thr Ala Thr Phe Asp Pro Lys Thr Asp
145                 150                 155                 160

Gln Phe Ile Ile His Ser Pro Thr Gln Thr Ser Ser Lys Trp Trp Pro
                165                 170                 175

Gly Gly Leu Gly Lys Val Ser Thr His Ala Val Ile Tyr Ala Arg Leu
            180                 185                 190

Ile Thr Asn Gly Lys Asp His Gly Val His Gly Phe Ile Val Gln Leu
        195                 200                 205

Arg Ser Leu Asp Asp His Ser Pro Leu Pro Gly Ile Thr Val Gly Asp
210                 215                 220

Ile Gly Met Lys Phe Gly Asn Gly Ala Tyr Asn Ser Met Asp Asn Gly
225                 230                 235                 240

Phe Leu Met Phe Asp His Phe Arg Ile Pro Arg Asp Gln Met Leu Met
                245                 250                 255

Arg Leu Leu Lys Val Thr Arg Glu Gly Lys Tyr Val Ala Ser Asp Val
            260                 265                 270

Pro Arg Gln Leu Val Tyr Gly Thr Met Val Tyr Val Arg Gln Ser Ile
        275                 280                 285

Val Ser Asn Ala Ser Thr Ala Leu Ala Arg Ala Val Cys Ile Ala Thr
290                 295                 300

Arg Tyr Ser Ala Val Arg Arg Gln Phe Gly Ser His Asp Gly Gly Ile
305                 310                 315                 320

Glu Thr Gln Val Ile Asp Tyr Lys Thr Gln Gln Asn Arg Leu Phe Pro
                325                 330                 335

Leu Leu Ala Ser Ala Tyr Ala Phe Arg Phe Val Gly Glu Trp Leu Lys
            340                 345                 350

Trp Leu Tyr Thr Asp Val Thr Lys Arg Leu Glu Ala Ser Asp Phe Ala
        355                 360                 365

Thr Leu Pro Glu Ala His Ala Cys Thr Ala Gly Leu Lys Ser Met Thr
```

```
          370                 375                 380
Thr Ser Ala Thr Ser Asp Gly Ile Glu Glu Cys Arg Lys Leu Cys Gly
385                 390                 395                 400
Gly His Gly Tyr Leu Trp Cys Ser Gly Leu Pro Glu Leu Phe Ala Val
                405                 410                 415
Tyr Val Pro Ala Cys Thr Tyr Glu Gly Asp Asn Val Val Leu Gln Leu
            420                 425                 430
Gln Val Ala Arg Phe Leu Met Lys Thr Val Ser Gln Leu Gly Ser Gly
        435                 440                 445
Lys Ala Pro Ser Gly Thr Thr Ala Tyr Met Gly Arg Ala Lys His Leu
450                 455                 460
Leu Gln Cys Ser Ser Gly Val Arg Asn Ala Arg Asp Trp Leu Asn Pro
465                 470                 475                 480
Gly Met Val Leu Glu Ser Phe Glu Ala Arg Ala Leu Arg Met Ala Val
                485                 490                 495
Thr Arg Ala Asn Asn Leu Ser Lys Phe Glu Asn Gln Glu Gln Gly Phe
            500                 505                 510
Ser Glu Leu Leu Ala Asp Leu Val Glu Ala Ala Thr Ala His Cys Gln
        515                 520                 525
Leu Ile Val Val Ser Lys Phe Ile Ala Lys Val Glu Gly Asp Ile Glu
530                 535                 540
Gly Lys Gly Val Lys Lys Gln Leu Lys Asn Leu Cys Tyr Met Tyr Ala
545                 550                 555                 560
Leu Tyr Leu Leu His Lys His Leu Gly Asp Phe Leu Ser Thr Asn Ser
                565                 570                 575
Val Thr Pro Glu Gln Ala Ser Leu Ala Asn Gln Gln Leu Arg Ser Leu
            580                 585                 590
Tyr Ser Gln Val Arg Pro Asn Ala Val Ala Leu Val Asp Ala Phe Asp
        595                 600                 605
Tyr Thr Asp Gln Tyr Leu Gly Ser Val Leu Gly Arg Tyr Asp Gly Asn
            610                 615                 620
Val Tyr Pro Lys Leu Phe Glu Glu Ala Leu Lys Asp Pro Leu Asn Asp
625                 630                 635                 640
Ser Val Val Pro Asp Gly Tyr Arg Glu Tyr Ile Arg Pro Leu Ile Lys
                645                 650                 655
Gln Arg Phe Arg Ser Ala Lys Leu
            660

<210> SEQ ID NO 5
<211> LENGTH: 2267
<212> TYPE: DNA
<213> ORGANISM: Arabidopsis sp.

<400> SEQUENCE: 5
cattgaaatg gaatcgcggc gagagaagaa tccgatgacg gaggaggaat ctgatgggct      60
aattgcggcg aggcggatcc aacgattgtc tttacaccta tctccctcct tgacgctgtc     120
gccgtcgtta ccgttggtgc agacggagac gtgttcggcg aggtcgaaga agctggatgt     180
caacggcgaa gctttgtcgc tgtatatgag aggaaaacat atagatatac aagagaaaat     240
tttcgacttt ttcaattccc gacccgattt gcagacgccg atcgagatct ccaaggatga     300
tcatcgggaa ttgtgtatga atcagcttat agggcttgtt agagaagctg ggtaaggcc      360 gtttaggtat gttgctgatg atcctgagaa gtatttcgca atcatggaag ctgttggaag     420
tgttgatatg tcccttggga ttaagatggg cgttcaatac agtctctggg gaggctctgt     480
```

```
gatcaattta gggactaaga agcatagaga caagtatttt gatggcattg acaatcttga    540
ttacaccggt tgctttgcca tgactgaatt acaccatggg tcaaatgtgc aaggtcttca    600
gaccacggcg acattcgatc cacttaaaga cgaatttgtg atcgatacac ctaatgatgg    660
agctatcaaa tggtggattg gaaatgctgc agttcatggg aagtttgcca ctgttttttgc   720 caggcttata cttccaactc atgattccaa aggagtctcg gatatgggtg ttcacgcctt    780
cattgttccg ataagggata tgaaaacaca ccagacactc cctggtgttg aaatccaaga    840
ttgtggacat aaagtgggac ttaatggagt ggataatggt gcgttgagat ccgttctgt     900 gagaataccc cgtgataatc ttctcaatcg ttttggagat gtgtcccgag atgggacgta    960
tacaagtagt ttgccaacaa tcaataaaag atttggtgca acactcggtg agcttgtagg   1020
tggtcgagtt ggccttgcct atgcatctgt tggcgtcctt aaaatctctg caacgattgc   1080
cattcgttat tctcttctaa gacaacaatt cgggcctcca agcaacctg aggtcagtat    1140 tctcgattac cagtctcaac aacacaagct catgccgatg ttagcctcca cctatgcata   1200
ccattttgca actgtatacc ttgtggagaa atattcagag atgaagaaga ctcacgatga   1260
gcaattggtt gctgatgtcc atgcactctc tgctgggctc aaatcttatg tgacgtctta   1320
caccgccaag gcgctctcgg tctgcagaga agcctgtgga ggtcatggtt acgcagctgt   1380
taaccgattt ggaagcttga gaaatgatca tgacattttc caaacatttg aaggagacaa   1440
cactgtactt ctgcaacagg tggctgctga tttattgaag cgttataaag aaaagttcca   1500
aggcgggaca ttgacagtta catggagcta cttgagagaa tcaatgaaca cttatttgtc   1560
tcagccaaat cccgttacag cgcgttggga aggtgaagat catctaagag atcctaaatt   1620
ccaactagat gctttccggt atcgaacatc gcgattgcta caaaatgtgg cagcgagatt   1680
gcagaagcat tcaaagactc ttggtggttt cggggcatgg aacagatgct tgaatcatct   1740
tttaacgctt gcagaatctc acattgaaac agtcattctt gccaagttca tcgaagctgt   1800
taaaaactgc ccggacccaa gtgcaaaagc tgctctgaaa ctagcatgtg atctttacgc   1860
attggaccga atctggaaag atataggaac gtaccgtaac gtggattatg tggcgcctaa   1920
caaagctaag gcgattcata aactgacaga gtatttgagt tttcaagtaa ggaatgtggc   1980
caaggaacta gtggatgcgt tcgagctccc tgatcatgtt actcgagcac caattgctat   2040
gcagtccgat gcttattccc agtatactca agttgttgga ttctaaaaac acaagaacaa   2100
aacatatatc atcacaatga tcttttaatt cgaagcaaaa aaaagatgaa aaacaattta   2160 caggggtac aaaagaatct gcagtccttt gtatgtgttt ttagttgttg tttgttttca    2220
caggagaata aaaaaaaaca gagtaataaa aatgtcattt ttttcgt               2267
```

<210> SEQ ID NO 6
<211> LENGTH: 683
<212> TYPE: PRT
<213> ORGANISM: Arabidopsis sp.

<400> SEQUENCE: 6

```
Met Thr Glu Glu Ser Asp Gly Leu Ile Ala Ala Arg Arg Ile Gln
 1               5                  10                  15

Arg Leu Ser Leu His Leu Ser Pro Ser Leu Thr Leu Ser Pro Ser Leu
            20                  25                  30

Pro Leu Val Gln Thr Glu Thr Cys Ser Ala Arg Ser Lys Lys Leu Asp
        35                  40                  45

Val Asn Gly Glu Ala Leu Ser Leu Tyr Met Arg Gly Lys His Ile Asp
```

-continued

```
            50                  55                  60
Ile Gln Glu Lys Ile Phe Asp Phe Phe Asn Ser Arg Pro Asp Leu Gln
 65                  70                  75                  80

Thr Pro Ile Glu Ile Ser Lys Asp Asp His Arg Glu Leu Cys Met Asn
                 85                  90                  95

Gln Leu Ile Gly Leu Val Arg Glu Ala Gly Val Arg Pro Phe Arg Tyr
                100                 105                 110

Val Ala Asp Asp Pro Glu Lys Tyr Phe Ala Ile Met Glu Ala Val Gly
                115                 120                 125

Ser Val Asp Met Ser Leu Gly Ile Lys Met Gly Val Gln Tyr Ser Leu
            130                 135                 140

Trp Gly Gly Ser Val Ile Asn Leu Gly Thr Lys Lys His Arg Asp Lys
145                 150                 155                 160

Tyr Phe Asp Gly Ile Asp Asn Leu Asp Tyr Thr Gly Cys Phe Ala Met
                165                 170                 175

Thr Glu Leu His His Gly Ser Asn Val Gln Gly Leu Gln Thr Thr Ala
                180                 185                 190

Thr Phe Asp Pro Leu Lys Asp Glu Phe Val Ile Asp Thr Pro Asn Asp
            195                 200                 205

Gly Ala Ile Lys Trp Trp Ile Gly Asn Ala Ala Val His Gly Lys Phe
210                 215                 220

Ala Thr Val Phe Ala Arg Leu Ile Leu Pro Thr His Asp Ser Lys Gly
225                 230                 235                 240

Val Ser Asp Met Gly Val His Ala Phe Ile Val Pro Ile Arg Asp Met
                245                 250                 255

Lys Thr His Gln Thr Leu Pro Gly Val Glu Ile Gln Asp Cys Gly His
            260                 265                 270

Lys Val Gly Leu Asn Gly Val Asp Asn Gly Ala Leu Arg Phe Arg Ser
            275                 280                 285

Val Arg Ile Pro Arg Asp Asn Leu Leu Asn Arg Phe Gly Asp Val Ser
            290                 295                 300

Arg Asp Gly Thr Tyr Thr Ser Ser Leu Pro Thr Ile Asn Lys Arg Phe
305                 310                 315                 320

Gly Ala Thr Leu Gly Glu Leu Val Gly Gly Arg Val Gly Leu Ala Tyr
                325                 330                 335

Ala Ser Val Gly Val Leu Lys Ile Ser Ala Thr Ile Ala Ile Arg Tyr
            340                 345                 350

Ser Leu Leu Arg Gln Gln Phe Gly Pro Pro Lys Gln Pro Glu Val Ser
            355                 360                 365

Ile Leu Asp Tyr Gln Ser Gln Gln His Lys Leu Met Pro Met Leu Ala
            370                 375                 380

Ser Thr Tyr Ala Tyr His Phe Ala Thr Val Tyr Leu Val Glu Lys Tyr
385                 390                 395                 400

Ser Glu Met Lys Lys Thr His Asp Glu Gln Leu Val Ala Asp Val His
                405                 410                 415

Ala Leu Ser Ala Gly Leu Lys Ser Tyr Val Thr Ser Tyr Thr Ala Lys
            420                 425                 430

Ala Leu Ser Val Cys Arg Glu Ala Cys Gly Gly His Gly Tyr Ala Ala
            435                 440                 445

Val Asn Arg Phe Gly Ser Leu Arg Asn Asp His Asp Ile Phe Gln Thr
            450                 455                 460

Phe Glu Gly Asp Asn Thr Val Leu Leu Gln Gln Val Ala Ala Asp Leu
465                 470                 475                 480
```

```
Leu Lys Arg Tyr Lys Glu Lys Phe Gln Gly Gly Thr Leu Thr Val Thr
                485                 490                 495

Trp Ser Tyr Leu Arg Glu Ser Met Asn Thr Tyr Leu Ser Gln Pro Asn
            500                 505                 510

Pro Val Thr Ala Arg Trp Glu Gly Glu Asp His Leu Arg Asp Pro Lys
        515                 520                 525

Phe Gln Leu Asp Ala Phe Arg Tyr Arg Thr Ser Arg Leu Leu Gln Asn
    530                 535                 540

Val Ala Ala Arg Leu Gln Lys His Ser Lys Thr Leu Gly Gly Phe Gly
545                 550                 555                 560

Ala Trp Asn Arg Cys Leu Asn His Leu Leu Thr Leu Ala Glu Ser His
                565                 570                 575

Ile Glu Thr Val Ile Leu Ala Lys Phe Ile Glu Ala Val Lys Asn Cys
            580                 585                 590

Pro Asp Pro Ser Ala Lys Ala Leu Lys Leu Ala Cys Asp Leu Tyr
        595                 600                 605

Ala Leu Asp Arg Ile Trp Lys Asp Ile Gly Thr Tyr Arg Asn Val Asp
    610                 615                 620

Tyr Val Ala Pro Asn Lys Ala Lys Ala Ile His Lys Leu Thr Glu Tyr
625                 630                 635                 640

Leu Ser Phe Gln Val Arg Asn Val Ala Lys Glu Leu Val Asp Ala Phe
                645                 650                 655

Glu Leu Pro Asp His Val Thr Arg Ala Pro Ile Ala Met Gln Ser Asp
            660                 665                 670

Ala Tyr Ser Gln Tyr Thr Gln Val Val Gly Phe
        675                 680

<210> SEQ ID NO 7
<211> LENGTH: 2025
<212> TYPE: DNA
<213> ORGANISM: Arabidopsis sp.

<400> SEQUENCE: 7
atgtcggata tcgtgcact ccgacgagct catgttctcg ccaatcacat actccaatca      60
aatcctccat cttcgaaccc gtccctgtcg cgcgaggtat gtttgcagta ctctccaccg    120
gagctcaacg agagctatgg attcgatgtc aaggagatga gaaaattact tgacggacac    180
aacgtggtgg atcgggactg gatttatgga ctcatgatgc agagcaatct gtttaatcgg    240
aaggagagag gaggtaagat tttcgtgtcg ccggattaca atcagacgat ggagcagcag    300
cgtgagatca caatgaaacg gatctggtac ttgcttgaga tgggtgttt caaaggatgg    360
ttgacggaga caggtcctga ggccgagctc aggaaattag ctctgcttga ggtttgcggg    420
atttatgatc actccgtctc catcaaagtt ggtgtgcatt cttcctgtg gggtaatgct    480
gtaaagtttt ttggaacaaa gcgtcaccat gaaaagtggc tgaagaacac cgaagattat    540
gttgtcaagg gctgttttgc aatgactgag ctaggccatg aagtaatgt acggggaatt    600
gaaacagtga caacttatga cccaaaaact gaagagtttg tgataaatac tccttgtgaa    660
tctgctcaga agtattggat tggtgggca gctaatcatg caacccacac aattgtgttt    720
tcacagcttc atatcaacgg aaccaaccag ggggtccatg cctttatcgc ccaaatcagg    780
gatcaagatg cagcatatg tccaaatatc cgcattgctg actgtggaca caaaattggt    840
ctaaatggtg ttgacaatgg ccggatctgg tttgataatc ttcgaattcc aagagagaat    900
ttgttgaatg cagttgctga tgtttcgtct gatgggaagt atgttagctc aattaaagat    960
```

-continued

```
cctgatcaga gatttggagc attcatggcc cctttgactt ctggccgagt cacaattgca    1020
tcaagtgcaa tttattctgc aaaggtcgga ttatctattg ctataaggta ctcattatcg    1080
agaagagcct tctctgttac agctaatggt cctgaagtcc tcctccttga ttacccaagc    1140
catcaaaggc gactgctacc actcctagca aagacatatg ctatgagttt tgctgcaaat    1200
gaattgaaga tgatttacgt gaagagaaca ccggagacca caaagccat ccacgttgtt     1260 tcaagtgggt tcaaagctgt tctcacctgg cacaatatgc acacacttca ggaatgtcga    1320
gaagctgtcg gagggcaagg tgtgaaaaca gaaaatctag ttggtcagtt gaaaggtgaa    1380
tttgatgtgc agactacatt tgagggtgac aataatgtat tgatgcagca ggtgagcaag    1440
gcgcttttcg ctgaatatgt atcgtgtaag aagagaaaca aacctttcaa gggactggga    1500
ttggagcaca tgaacagtcc acgtcctgta ttactgactc aactcacatc atcaaccctc    1560
agatgcagcc aattccagac aaatgcgttc tgcttaagag agcgagatct tctggagcaa    1620
tttacttctg aagttgcaca gcttcaaggg agaggagaaa gtcgagaatt ctctttcctc    1680
stgagtcatc aacttgctga agacttaggt aaagctttca cagagaaagc aatacttcaa    1740 accatttttgg atgctgaggc aaaactacct actggctcag taaaggatgt gttgggtctt    1800
gtaagatcaa tgtacgcatt gatcagcttg gaagaagatc catcgttgct gcgatatggt    1860
tacctatctc aggataatgt tggagatgtg aggagagaag tttcaaagct ctgtggagag    1920
cttagaccac acgcgcttgc actcgtcact tcattcggca ttccagactc cttcttgagt    1980
ccaattgcat tcaactgggt cgaagccaat gcttggtctt cagtt                    2025
```

<210> SEQ ID NO 8
<211> LENGTH: 675
<212> TYPE: PRT
<213> ORGANISM: Arabidopsis sp.
<220> FEATURE:
<221> NAME/KEY: VARIANT
<222> LOCATION: (1)...(675)
<223> OTHER INFORMATION: Xaa = Any Amino Acid

<400> SEQUENCE: 8

```
Met Ser Asp Asn Arg Ala Leu Arg Arg Ala His Val Leu Ala Asn His
 1               5                  10                  15

Ile Leu Gln Ser Asn Pro Pro Ser Ser Asn Pro Ser Leu Ser Arg Glu
                20                  25                  30

Val Cys Leu Gln Tyr Ser Pro Pro Glu Leu Asn Glu Ser Tyr Gly Phe
            35                  40                  45

Asp Val Lys Glu Met Arg Lys Leu Leu Asp Gly His Asn Val Val Asp
        50                  55                  60

Arg Asp Trp Ile Tyr Gly Leu Met Met Gln Ser Asn Leu Phe Asn Arg
 65                  70                  75                  80

Lys Glu Arg Gly Gly Lys Ile Phe Val Ser Pro Asp Tyr Asn Gln Thr
                85                  90                  95

Met Glu Gln Gln Arg Glu Ile Thr Met Lys Arg Ile Trp Tyr Leu Leu
            100                 105                 110

Glu Asn Gly Val Phe Lys Gly Trp Leu Thr Glu Thr Gly Pro Glu Ala
        115                 120                 125

Glu Leu Arg Lys Leu Ala Leu Leu Glu Val Cys Gly Ile Tyr Asp His
    130                 135                 140

Ser Val Ser Ile Lys Val Gly Val His Phe Phe Leu Trp Gly Asn Ala
145                 150                 155                 160
```

-continued

```
Val Lys Phe Phe Gly Thr Lys Arg His His Glu Lys Trp Leu Lys Asn
                165                 170                 175
Thr Glu Asp Tyr Val Val Lys Gly Cys Phe Ala Met Thr Glu Leu Gly
            180                 185                 190
His Gly Ser Asn Val Arg Gly Ile Glu Thr Val Thr Thr Tyr Asp Pro
        195                 200                 205
Lys Thr Glu Glu Phe Val Ile Asn Thr Pro Cys Glu Ser Ala Gln Lys
    210                 215                 220
Tyr Trp Ile Gly Gly Ala Ala Asn His Ala Thr His Thr Ile Val Phe
225                 230                 235                 240
Ser Gln Leu His Ile Asn Gly Thr Asn Gln Gly Val His Ala Phe Ile
                245                 250                 255
Ala Gln Ile Arg Asp Gln Asp Gly Ser Ile Cys Pro Asn Ile Arg Ile
            260                 265                 270
Ala Asp Cys Gly His Lys Ile Gly Leu Asn Gly Val Asp Asn Gly Arg
        275                 280                 285
Ile Trp Phe Asp Asn Leu Arg Ile Pro Arg Glu Asn Leu Leu Asn Ala
    290                 295                 300
Val Ala Asp Val Ser Ser Asp Gly Lys Tyr Val Ser Ser Ile Lys Asp
305                 310                 315                 320
Pro Asp Gln Arg Phe Gly Ala Phe Met Ala Pro Leu Thr Ser Gly Arg
                325                 330                 335
Val Thr Ile Ala Ser Ser Ala Ile Tyr Ser Ala Lys Val Gly Leu Ser
            340                 345                 350
Ile Ala Ile Arg Tyr Ser Leu Ser Arg Arg Ala Phe Ser Val Thr Ala
        355                 360                 365
Asn Gly Pro Glu Val Leu Leu Asp Tyr Pro Ser His Gln Arg Arg
    370                 375                 380
Leu Leu Pro Leu Leu Ala Lys Thr Tyr Ala Met Ser Phe Ala Ala Asn
385                 390                 395                 400
Glu Leu Lys Met Ile Tyr Val Lys Arg Thr Pro Glu Thr Asn Lys Ala
                405                 410                 415
Ile His Val Val Ser Ser Gly Phe Lys Ala Val Leu Thr Trp His Asn
            420                 425                 430
Met His Thr Leu Gln Glu Cys Arg Glu Ala Val Gly Gly Gln Gly Val
        435                 440                 445
Lys Thr Glu Asn Leu Val Gly Gln Leu Lys Gly Glu Phe Asp Val Gln
    450                 455                 460
Thr Thr Phe Glu Gly Asp Asn Asn Val Leu Met Gln Gln Val Ser Lys
465                 470                 475                 480
Ala Leu Phe Ala Glu Tyr Val Ser Cys Lys Lys Arg Asn Lys Pro Phe
                485                 490                 495
Lys Gly Leu Gly Leu Glu His Met Asn Ser Pro Arg Pro Val Leu Leu
            500                 505                 510
Thr Gln Leu Thr Ser Ser Thr Leu Arg Cys Ser Gln Phe Gln Thr Asn
        515                 520                 525
Ala Phe Cys Leu Arg Glu Arg Asp Leu Leu Glu Gln Phe Thr Ser Glu
    530                 535                 540
Val Ala Gln Leu Gln Gly Arg Gly Glu Ser Arg Glu Phe Ser Phe Leu
545                 550                 555                 560
Xaa Ser His Gln Leu Ala Glu Asp Leu Gly Lys Ala Phe Thr Glu Lys
                565                 570                 575
Ala Ile Leu Gln Thr Ile Leu Asp Ala Glu Ala Lys Leu Pro Thr Gly
```

|  | 580 |  |  |  |  | 585 |  |  |  | 590 |  |  |
|---|---|---|---|---|---|---|---|---|---|---|---|---|
| Ser | Val | Lys | Asp | Val | Leu | Gly | Leu | Val | Arg | Ser | Met | Tyr | Ala | Leu | Ile |
|  |  | 595 |  |  |  | 600 |  |  |  | 605 |  |  |

Ser Leu Glu Glu Asp Pro Ser Leu Leu Arg Tyr Gly Tyr Leu Ser Gln
    610                     615                 620

Asp Asn Val Gly Asp Val Arg Arg Glu Val Ser Lys Leu Cys Gly Glu
625                 630                 635                 640

Leu Arg Pro His Ala Leu Ala Leu Val Thr Ser Phe Gly Ile Pro Asp
                645                 650                 655

Ser Phe Leu Ser Pro Ile Ala Phe Asn Trp Val Glu Ala Asn Ala Trp
            660                 665                 670

Ser Ser Val
        675

<210> SEQ ID NO 9
<211> LENGTH: 1579
<212> TYPE: DNA
<213> ORGANISM: Arabidopsis sp.

<400> SEQUENCE: 9

```
caatttctcc gtcactatca taaccatggc ggtgctttca tctgcagatc gagctagtaa      60
tgagaagaag gtgaagagtt catactttga tttgccacct atggaaatgt ctgtagcatt     120
tcctcaagca actccagcct ctacatttcc accttgtact tcagactatt atcatttcaa     180
tgatctactg actccggaag aacaagctat ccggaagaaa gtgagggaat gcatggagaa     240
agaagttgct ccaataatga cagagtactg ggagaaagca gaatttccat tccatatcac     300
tccaaagctt ggggctatgg gtgttgctgg tggctcgatc aagggttatg gatgtcctgg     360
tctctccatc accgccaatg caattgccac agcagaaata gctagagttg atgcaagttg     420
ttcgactttc attttggtgc attcttcttt gggcatgctc actattgcac tctgtggatc     480
agaagcacag aaggagaagt atttgccttc tttggctcaa ttgaatactg tggcttgttg     540
ggctttgaca gagcccgaca atggaagcga tgcaagtggt ctaggaacga ctgcaacaaa     600
ggttgaagga ggttggaaaa ttaatggaca aaagcgttgg attggaaaca gcacctttgc     660
agatctgttg atcatctttg cgaggaatac aacaactaac caaatcaacg gattcatagt     720
caagaaagat gcgcctggcc taaaggctac taagatccca aataaaatag gtttacgtat     780
ggttcaaaat ggagatattc tactacagaa tgtctttgtt ccagatgagg atcggttacc     840
tggggtaaat tctttcagg acaccagcaa ggttctggct gtctcacgtg taatggtggc     900
ctggcaacca atcggcatat caatgggaat ctacgatatg tgccacaggt atctgaagga     960
gaggaaacag tttggagcac cgttggctgc tttccagtta aaccaacaga gcttgtgca    1020
gatgctgggt aacgttcaag cgatgtttct aatgggttgg cgtctctgca agctgtatga    1080
gacgggtcag atgactccag gtcaagccag tttaggaaag gcatggattt catcaaaagc    1140
gagagaaact gcttcgctag gtcgggaatt acttggtggg aatggaattc tagcagattt    1200
tctggtagca aaggctttct gtgaccttga acccatttat acatacgaag ggacttatga    1260
tataaacacc ttagtaacag ggagggaagt aacgggtatt gcgagtttca aaccggctac    1320
acgtagccgt ctctaagtta aaaggttgtc cattgtttgt tgttgtctgt tggttagtat    1380
tgatattgtg atgtggggtt tacatctaca aatgtgccaa ataatctgac ccaaaaagat    1440
ttagggtcca atgggggaat aatatcgttg ttgcaaaact taatccagtt attgcttctt    1500
gcaatatgga ttcgtcttgt ggcttgtact gggggaaata ccatttgtta acctttatt    1560
```
aattcaaatt gccaatgtc          1579

<210> SEQ ID NO 10
<211> LENGTH: 436
<212> TYPE: PRT
<213> ORGANISM: Arabidopsis sp.

<400> SEQUENCE: 10

| Met | Ala | Val | Leu | Ser | Ser | Ala | Asp | Arg | Ala | Ser | Asn | Glu | Lys | Lys | Val |
|---|---|---|---|---|---|---|---|---|---|---|---|---|---|---|---|
| 1 | | | | 5 | | | | | 10 | | | | | 15 | |

Lys Ser Ser Tyr Phe Asp Leu Pro Met Glu Met Ser Val Ala Phe
                20                  25                  30

Pro Gln Ala Thr Pro Ala Ser Thr Phe Pro Pro Cys Thr Ser Asp Tyr
            35                  40                  45

Tyr His Phe Asn Asp Leu Leu Thr Pro Glu Glu Gln Ala Ile Arg Lys
 50                  55                  60

Lys Val Arg Glu Cys Met Glu Lys Glu Val Ala Pro Ile Met Thr Glu
65                  70                  75                  80

Tyr Trp Glu Lys Ala Glu Phe Pro Phe His Ile Thr Pro Lys Leu Gly
                85                  90                  95

Ala Met Gly Val Ala Gly Gly Ser Ile Lys Gly Tyr Gly Cys Pro Gly
            100                 105                 110

Leu Ser Ile Thr Ala Asn Ala Ile Ala Thr Ala Glu Ile Ala Arg Val
        115                 120                 125

Asp Ala Ser Cys Ser Thr Phe Ile Leu Val His Ser Ser Leu Gly Met
    130                 135                 140

Leu Thr Ile Ala Leu Cys Gly Ser Glu Ala Gln Lys Glu Lys Tyr Leu
145                 150                 155                 160

Pro Ser Leu Ala Gln Leu Asn Thr Val Ala Cys Trp Ala Leu Thr Glu
                165                 170                 175

Pro Asp Asn Gly Ser Asp Ala Ser Gly Leu Gly Thr Thr Ala Thr Lys
            180                 185                 190

Val Glu Gly Gly Trp Lys Ile Asn Gly Gln Lys Arg Trp Ile Gly Asn
        195                 200                 205

Ser Thr Phe Ala Asp Leu Leu Ile Ile Phe Ala Arg Asn Thr Thr Thr
    210                 215                 220

Asn Gln Ile Asn Gly Phe Ile Val Lys Lys Asp Ala Pro Gly Leu Lys
225                 230                 235                 240

Ala Thr Lys Ile Pro Asn Lys Ile Gly Leu Arg Met Val Gln Asn Gly
                245                 250                 255

Asp Ile Leu Leu Gln Asn Val Phe Val Pro Asp Glu Asp Arg Leu Pro
            260                 265                 270

Gly Val Asn Ser Phe Gln Asp Thr Ser Lys Val Leu Ala Val Ser Arg
        275                 280                 285

Val Met Val Ala Trp Gln Pro Ile Gly Ile Ser Met Gly Ile Tyr Asp
    290                 295                 300

Met Cys His Arg Tyr Leu Lys Glu Arg Lys Gln Phe Gly Ala Pro Leu
305                 310                 315                 320

Ala Ala Phe Gln Leu Asn Gln Gln Lys Leu Val Gln Met Leu Gly Asn
                325                 330                 335

Val Gln Ala Met Phe Leu Met Gly Trp Arg Leu Cys Lys Leu Tyr Glu
            340                 345                 350

Thr Gly Gln Met Thr Pro Gly Gln Ala Ser Leu Gly Lys Ala Trp Ile
        355                 360                 365

```
Ser Ser Lys Ala Arg Glu Thr Ala Ser Leu Gly Arg Glu Leu Leu Gly
    370                 375                 380

Gly Asn Gly Ile Leu Ala Asp Phe Leu Val Ala Lys Ala Phe Cys Asp
385                 390                 395                 400

Leu Glu Pro Ile Tyr Thr Tyr Glu Gly Thr Tyr Asp Ile Asn Thr Leu
                405                 410                 415

Val Thr Gly Arg Glu Val Thr Gly Ile Ala Ser Phe Lys Pro Ala Thr
                420                 425                 430

Arg Ser Arg Leu
        435

<210> SEQ ID NO 11
<211> LENGTH: 1765
<212> TYPE: DNA
<213> ORGANISM: Arabidopsis sp.

<400> SEQUENCE: 11
accttataaa tgatcacaaa cccgaggact gtgagttttc gtgtagaaca atccttctc      60
tgagaaaaaa caacagatcc gaattttatc tttaatcagc cggaaaaaat ggagaaagcg     120
atcgagagac aacgcgttct tcttgagcat ctccgacctt cttcttcttc ttcgcacaat    180
tacgaggctt ctctatctgc ttctgcttgc ttggctgggg acagtgctgc atatcagagg    240
acctctctct atggagatga tgttgtcatt gtcgcggcac ataggactcc actatgcaag    300
tccaaacgtg gcaatttcaa ggatacatat cccgatgatt gctcgcacc tgttttgagg     360
gcattgatag agaagacgaa tctaaaccca agtgaagtag gtgacattgt tgtgggtact    420
gttttggcac ctggatctca gagagccagt gaatgcagga tggctgcgtt ctatgctggt    480
ttccctgaaa ccgtggctgt cagaactgtg aatagacagt gctcatctgg gcttcaggct    540
gttgctgatg tagccgctgc cattaaagcg ggattttatg acattggtat cggggctggt    600
ttggagtcca tgactaccaa tccaatggca tgggaagggt cagtcaaccc agcggtgaag    660
aagtttgcac aagcgcagaa ttgtcttctt cctatgggtg ttacgtcaga aaatgtagca    720
caacgctttg gtgtctcaag gcaggagcaa gatcaagctg ctgttgactc gcacagaaag    780
gcagctgctg ctactgctgc tggtaaattc aaggatgaga tcattcctgt taagaccaag    840
cttgttgacc gaagactggt gatgagaaa cccattacag tttctgttga tgatggtatc    900
cgaccaacca caactcttgc ttctcttggg aagctgaagc cagtgtttaa gaaggatggc    960
accactactg ctggaaaattc cagccaagta agtgatggtg caggagcggt tctcctaatg   1020
aagagaagtg ttgcaatgca aaaggactt cccgttcttg gtgtattcag gacatttgct    1080
gcagttggtg ttgaccctgc aatcatgggt atcggtccag cagttgccat tcctgctgca    1140
gttaaggcgg ctggtttaga acttgatgac atcgacttgt tgagatcaa tgaggcattt     1200
gcatctcagt ttgtttattg ccgtaacaaa ttgggacttg acccagagaa atcaatgtc     1260
aacggaggtg caatggccat aggccatcct tgggcgcta caggagcgcg ttgtgttgct    1320
acattgttgc acgagatgaa acgccgtggt aaagactgcc gttttggagt agtgtcaatg   1380
tgcattggga cggggatggg tgcagcagct gtgtttgaga gaggagatgg agttgatgag   1440
cttcgcaacg caaggaaagt tgaagcgcaa ggtcttttgt ccaaggacgc tcgctagaga   1500
ggaccatgca ccaaaaccgt ttttcacctc acctctctct tttctggtct tcttgtcact   1560
ttcttcagat attattatag tttcgaataa agcacacaac caatgtttgc ctgagtcttg   1620
tgttgttctt gaccaggtca tgtgtttagt atttttttta agtgaagggg gataatcttt   1680
```

-continued

```
aaatctttta tatgtaagaa tattgttctt ctcgaatttc atcagttgtt gcttctagaa    1740
attttagatt ttttgggtgg cagcc                                          1765
```

<210> SEQ ID NO 12
<211> LENGTH: 462
<212> TYPE: PRT
<213> ORGANISM: Arabidopsis sp.

<400> SEQUENCE: 12

```
Met Glu Lys Ala Ile Glu Arg Gln Arg Val Leu Leu Glu His Leu Arg
 1               5                  10                  15

Pro Ser Ser Ser Ser His Asn Tyr Glu Ala Ser Leu Ser Ala Ser
                20                  25                  30

Ala Cys Leu Ala Gly Asp Ser Ala Ala Tyr Gln Arg Thr Ser Leu Tyr
            35                  40                  45

Gly Asp Asp Val Val Ile Val Ala Ala His Arg Thr Pro Leu Cys Lys
        50                  55                  60

Ser Lys Arg Gly Asn Phe Lys Asp Thr Tyr Pro Asp Asp Leu Leu Ala
65                  70                  75                  80

Pro Val Leu Arg Ala Leu Ile Glu Lys Thr Asn Leu Asn Pro Ser Glu
                85                  90                  95

Val Gly Asp Ile Val Val Gly Thr Val Leu Ala Pro Gly Ser Gln Arg
            100                 105                 110

Ala Ser Glu Cys Arg Met Ala Ala Phe Tyr Ala Gly Phe Pro Glu Thr
        115                 120                 125

Val Ala Val Arg Thr Val Asn Arg Gln Cys Ser Ser Gly Leu Gln Ala
130                 135                 140

Val Ala Asp Val Ala Ala Ala Ile Lys Ala Gly Phe Tyr Asp Ile Gly
145                 150                 155                 160

Ile Gly Ala Gly Leu Glu Ser Met Thr Thr Asn Pro Met Ala Trp Glu
                165                 170                 175

Gly Ser Val Asn Pro Ala Val Lys Lys Phe Ala Gln Ala Gln Asn Cys
            180                 185                 190

Leu Leu Pro Met Gly Val Thr Ser Glu Asn Val Ala Gln Arg Phe Gly
        195                 200                 205

Val Ser Arg Gln Glu Gln Asp Gln Ala Ala Val Asp Ser His Arg Lys
210                 215                 220

Ala Ala Ala Ala Thr Ala Ala Gly Lys Phe Lys Asp Glu Ile Ile Pro
225                 230                 235                 240

Val Lys Thr Lys Leu Val Asp Pro Lys Thr Gly Asp Glu Lys Pro Ile
                245                 250                 255

Thr Val Ser Val Asp Asp Gly Ile Arg Pro Thr Thr Thr Leu Ala Ser
            260                 265                 270

Leu Gly Lys Leu Lys Pro Val Phe Lys Lys Asp Gly Thr Thr Thr Ala
        275                 280                 285

Gly Asn Ser Ser Gln Val Ser Asp Gly Ala Gly Ala Val Leu Leu Met
290                 295                 300

Lys Arg Ser Val Ala Met Gln Lys Gly Leu Pro Val Leu Gly Val Phe
305                 310                 315                 320

Arg Thr Phe Ala Ala Val Gly Val Asp Pro Ala Ile Met Gly Ile Gly
                325                 330                 335

Pro Ala Val Ala Ile Pro Ala Ala Val Lys Ala Ala Gly Leu Glu Leu
            340                 345                 350
```

-continued

```
Asp Asp Ile Asp Leu Phe Glu Ile Asn Glu Ala Phe Ala Ser Gln Phe
            355                 360                 365
Val Tyr Cys Arg Asn Lys Leu Gly Leu Asp Pro Glu Lys Ile Asn Val
        370                 375                 380
Asn Gly Gly Ala Met Ala Ile Gly His Pro Leu Gly Ala Thr Gly Ala
385                 390                 395                 400
Arg Cys Val Ala Thr Leu Leu His Glu Met Lys Arg Gly Lys Asp
                405                 410                 415
Cys Arg Phe Gly Val Val Ser Met Cys Ile Gly Thr Gly Met Gly Ala
            420                 425                 430
Ala Ala Val Phe Glu Arg Gly Asp Gly Val Asp Glu Leu Arg Asn Ala
        435                 440                 445
Arg Lys Val Glu Ala Gln Gly Leu Leu Ser Lys Asp Ala Arg
    450                 455                 460
```

<210> SEQ ID NO 13
<211> LENGTH: 1677
<212> TYPE: DNA
<213> ORGANISM: Arabidopsis sp.

<400> SEQUENCE: 13

```
gccctctaga tgcatgctcg agcggccgcc agtgtgatgg atatctgcag aattcgccct    60
tagatctcaa aataatcaaa cgaaaacaat ggaaaaagca acggagagac aaaggatact   120
gcttcgtcat cttcaacctt cgtcatcttc gacgcctct ctctctgcct cagcttgctt    180
gtccaaagac agtgctgcat atcaatatgg agatgatgtt gtcattgtcg cggcacaaag   240
gactgcactt tgcaaggcaa aacgtggcag cttcaaggat acatttccag cgagttgct    300
tgcctctgta ttgagagcat tgatagagaa aactaatgta aacccaagtg aagttggtga   360
cattgtagtg ggtactgttt tgggaccagg atctcagaga gccagtgaat gcaggatggc   420
tgcgttctat gctggtttcc ccgaaactgt tcccatcaga accgtgaaca gacagtgttc   480
atctgggctt caggctgttg ctgatgttgc cgctgccata aaagctggtt tttatgacat   540
tggtattgga gctgggctgg agtccatgac aactaatcca aggggatgga aaggatcagt   600
caacccaaat gtgaagaagt tgaacaagc tcacaattgc cttcttccaa tgggtattac    660
ttcagaaaat gtagcacacc ggtttaatgt tcaaggagag agcaggatc aagctgctgt    720
tgattctcac agaaaggctg cttctgctac tgcttccggt aaatttaagg atgagataac   780
ccctgtaaaa accaagattg ttgacccaaa gacaggtgat gagaaaccca taacagttc    840
tgtggatgat gggattcgac taacacaac ccttccgga cttgcaaagc tgaagccagt    900
gtttaaggaa gacggaacca aactgctgg gaattctagc caattaagtg acggtgctgg   960
agctgttctc cttatgagga gaaatgtcgc aatgcagaaa ggccttccca ttcttggtgt    1020
attcaggaca ttttctgcag ttggtgtgga cccagccatc atgggggttg gccagccgt   1080
tgccattcct gctgcagtca aggcagctgg tttagaactc aatgacgtcg acttgtttga   1140
gattaacgag gcatttgcat ctcagtttgt ttattgtcgg aacaagctcg ggctagacgc   1200
ggaaaagatc aatgtcaatg gaggagccat agccattgga catcccttgg gcgctacagg   1260
agccagatgc gttgcgacgc tgctgcatga gatgaaacga cgtggtaaag actgtcgttt   1320
tggcgtagtg tcaatgtgta taggttcggg aatgggagca gccgctgtgt ttgagagagg   1380
aggcggtgtg gatgagctct gtgatgtccg gaaagtctaa tgacaataag gccttttgac   1440
caaggaccct agctaaggac caaattagaa cacagtacta caaataaaca ttatcacaaa   1500
```

```
taaatgcgtt ctagatgaat aaatcataac gatagtacaa tacatgaggg aaaacttctt    1560 gttattttt aactctcttt tgttatatgg ttggaatata tacagatact ctttgctcga    1620
gaagggcgaa ttccagcaca ctggcggccg ttactagtgg atccgagctc ggtacca      1677
```

<210> SEQ ID NO 14
<211> LENGTH: 443
<212> TYPE: PRT
<213> ORGANISM: Arabidopsis sp.

<400> SEQUENCE: 14

```
Met Glu Lys Ala Thr Glu Arg Gln Arg Ile Leu Leu Arg His Leu Gln
 1               5                  10                  15

Pro Ser Ser Ser Asp Ala Ser Leu Ser Ala Ser Ala Cys Leu Ser
            20                  25                  30

Lys Asp Ser Ala Ala Tyr Gln Tyr Gly Asp Asp Val Val Ile Val Ala
        35                  40                  45

Ala Gln Arg Thr Ala Leu Cys Lys Ala Lys Arg Gly Ser Phe Lys Asp
    50                  55                  60

Thr Phe Pro Asp Glu Leu Leu Ala Ser Val Leu Arg Ala Leu Ile Glu
65                  70                  75                  80

Lys Thr Asn Val Asn Pro Ser Glu Val Gly Asp Ile Val Val Gly Thr
                85                  90                  95

Val Leu Gly Pro Gly Ser Gln Arg Ala Ser Glu Cys Arg Met Ala Ala
           100                 105                 110

Phe Tyr Ala Gly Phe Pro Glu Thr Val Pro Ile Arg Thr Val Asn Arg
       115                 120                 125

Gln Cys Ser Ser Gly Leu Gln Ala Val Ala Asp Val Ala Ala Ala Ile
   130                 135                 140

Lys Ala Gly Phe Tyr Asp Ile Gly Ile Gly Ala Gly Leu Glu Ser Met
145                 150                 155                 160

Thr Thr Asn Pro Arg Gly Trp Lys Gly Ser Val Asn Pro Asn Val Lys
                165                 170                 175

Lys Phe Glu Gln Ala His Asn Cys Leu Leu Pro Met Gly Ile Thr Ser
           180                 185                 190

Glu Asn Val Ala His Arg Phe Asn Val Ser Arg Glu Glu Gln Asp Gln
       195                 200                 205

Ala Ala Val Asp Ser His Arg Lys Ala Ala Ser Ala Thr Ala Ser Gly
   210                 215                 220

Lys Phe Lys Asp Glu Ile Thr Pro Val Lys Thr Lys Ile Val Asp Pro
225                 230                 235                 240

Lys Thr Gly Asp Glu Lys Pro Ile Thr Val Ser Val Asp Asp Gly Ile
                245                 250                 255

Arg Pro Asn Thr Thr Leu Ser Gly Leu Ala Lys Leu Lys Pro Val Phe
           260                 265                 270

Lys Glu Asp Gly Thr Thr Thr Ala Gly Asn Ser Ser Gln Leu Ser Asp
       275                 280                 285

Gly Ala Gly Ala Val Leu Leu Met Arg Arg Asn Val Ala Met Gln Lys
   290                 295                 300

Gly Leu Pro Ile Leu Gly Val Phe Arg Thr Phe Ser Ala Val Gly Val
305                 310                 315                 320

Asp Pro Ala Ile Met Gly Val Gly Pro Ala Val Ala Ile Pro Ala Ala
                325                 330                 335

Val Lys Ala Ala Gly Leu Glu Leu Asn Asp Val Asp Leu Phe Glu Ile
           340                 345                 350
```

Asn Glu Ala Phe Ala Ser Gln Phe Val Tyr Cys Arg Asn Lys Leu Gly
                355                 360                 365

Leu Asp Ala Glu Lys Ile Asn Val Asn Gly Gly Ala Ile Ala Ile Gly
        370                 375                 380

His Pro Leu Gly Ala Thr Gly Ala Arg Cys Val Ala Thr Leu Leu His
385                 390                 395                 400

Glu Met Lys Arg Gly Lys Asp Cys Arg Phe Gly Val Val Ser Met
                405                 410                 415

Cys Ile Gly Ser Gly Met Gly Ala Ala Ala Val Phe Glu Arg Gly Gly
                420                 425                 430

Gly Val Asp Glu Leu Cys Asp Val Arg Lys Val
            435                 440

<210> SEQ ID NO 15
<211> LENGTH: 1691
<212> TYPE: DNA
<213> ORGANISM: Arabidopsis sp.

<400> SEQUENCE: 15

| | | |
|---|---|---|
| tgagaacgat cgatcaaaaa tctctcccac gataaaaatg aggaccctga agctcattgt | 60 |
| acttaacgtc ttcccctttc cagaaaaatc aaccaaaccc atttcagttt ccccggaaag | 120 |
| tttttgtctt tcaatcacca ttagaattca gctgcaacac aagtgtttgc aacagagaga | 180 |
| atcatggaga gagctatgga agacaaaag atattgcttc gtcatctcaa tccagttttct | 240 |
| tcttctaatt cttctcttaa acatgaacct tctcttctgt ctcctgtgaa ttgtgtttct | 300 |
| gaagtttccc caatggctgc ttttggagat gacattgtga ttgtagcggc atatcgtacc | 360 |
| gccatttgca aagcgagacg tggaggtttc aaagacactc ttcctgatga tcttcttgct | 420 |
| tctgttctta aggctgtagt ggaaagaaca tctttggatc caagtgaagt tggtgatatc | 480 |
| gttgttggta ccgtgatagc gcctggttct cagagagcaa tggagtgtag agttgcagct | 540 |
| tattttgctg gttttcctga ctccgtgcca gttagaactg tcaatagaca atgctcatca | 600 |
| ggactacaag cagttgctga tgttgctgct tccattagag ctggttatta cgacattggt | 660 |
| attggtgctg gagtggaatc aatgtcaact gatcatattc ctggaggcgg ctttcatggc | 720 |
| tctaatccaa gagcacagga tttcccaaaa gcccgtgatt gtttgcttcc aatgggaatt | 780 |
| acttctgaaa acgttgcaga aaggttcggt gtcacaagag aagagcaaga tatggctgcg | 840 |
| gtggagtctc acaaacgcgc tgcagctgca atcgcgtctg gtaaactcaa ggatgaaatc | 900 |
| attcctgttg ctactaagat tgtggaccct gagactaaag cagagaaggc aatcgtcgta | 960 |
| tctgttgatg acggtgtacg tccaaactca aacatggcag atttggcaaa gctgaagact | 1020 |
| gtctttaaac agaacggttc caccacagct ggcaatgcta gtcagatcag tgatggtgct | 1080 |
| ggagcagtac tgctaatgaa gagaagtttg gctatgaaga agggacttcc cattcttgga | 1140 |
| gtattcagga gttttgctgt tactggtgtg gaaccatctg taatgggtat tggtccagct | 1200 |
| gttgccattc ccgctgcaac taagctcgca gggctcaacg tcagcgatat tgatctattc | 1260 |
| gagatcaatg aggcatttgc atctcagtat gtgtactctt gcaagaagtt agagctggat | 1320 |
| atggaaaagg tcaatgttaa tggaggagcc attgctattg ccatcccct gggtgctaca | 1380 |
| ggagctcgat gtgttgcgac attgttgcac gagatgaagc ggagaggaaa agattgccgc | 1440 |
| tttggagtaa tctcaatgtg cataggcact ggaatgggag ctgcagctgt ttttgagagg | 1500 |
| ggagactctg ttgataactt gtccaacgct cgtgtggcta acgggatag tcattagaac | 1560 |

```
atcgaagaga gcttgaataa gtagaagtaa tgatgcattg agtctaataa atatgatgct    1620
ttagctcttt cacattgctg aacaatgaaa acttttgtca ttctgagttt aaaatcaact    1680
acttttctct g                                                        1691
```

<210> SEQ ID NO 16
<211> LENGTH: 457
<212> TYPE: PRT
<213> ORGANISM: Arabidopsis sp.

<400> SEQUENCE: 16

```
Met Glu Arg Ala Met Glu Arg Gln Lys Ile Leu Leu Arg His Leu Asn
 1               5                  10                  15

Pro Val Ser Ser Asn Ser Ser Leu Lys His Glu Pro Ser Leu Leu
            20                  25                  30

Ser Pro Val Asn Cys Val Ser Glu Val Ser Pro Met Ala Ala Phe Gly
        35                  40                  45

Asp Asp Ile Val Ile Val Ala Ala Tyr Arg Thr Ala Ile Cys Lys Ala
    50                  55                  60

Arg Arg Gly Gly Phe Lys Asp Thr Leu Pro Asp Asp Leu Leu Ala Ser
65                  70                  75                  80

Val Leu Lys Ala Val Glu Arg Thr Ser Leu Asp Pro Ser Glu Val
                85                  90                  95

Gly Asp Ile Val Val Gly Thr Val Ile Ala Pro Gly Ser Gln Arg Ala
            100                 105                 110

Met Glu Cys Arg Val Ala Ala Tyr Phe Ala Gly Phe Pro Asp Ser Val
        115                 120                 125

Pro Val Arg Thr Val Asn Arg Gln Cys Ser Ser Gly Leu Gln Ala Val
    130                 135                 140

Ala Asp Val Ala Ala Ser Ile Arg Ala Gly Tyr Tyr Asp Ile Gly Ile
145                 150                 155                 160

Gly Ala Gly Val Glu Ser Met Ser Thr Asp His Ile Pro Gly Gly Gly
                165                 170                 175

Phe His Gly Ser Asn Pro Arg Ala Gln Asp Phe Pro Lys Ala Arg Asp
            180                 185                 190

Cys Leu Leu Pro Met Gly Ile Thr Ser Glu Asn Val Ala Glu Arg Phe
        195                 200                 205

Gly Val Thr Arg Glu Glu Gln Asp Met Ala Val Glu Ser His Lys
    210                 215                 220

Arg Ala Ala Ala Ile Ala Ser Gly Lys Leu Lys Asp Glu Ile Ile
225                 230                 235                 240

Pro Val Ala Thr Lys Ile Val Asp Pro Glu Thr Lys Ala Glu Lys Ala
                245                 250                 255

Ile Val Val Ser Val Asp Asp Gly Val Arg Pro Asn Ser Asn Met Ala
            260                 265                 270

Asp Leu Ala Lys Leu Lys Thr Val Phe Lys Gln Asn Gly Ser Thr Thr
        275                 280                 285

Ala Gly Asn Ala Ser Gln Ile Ser Asp Gly Ala Gly Ala Val Leu Leu
    290                 295                 300

Met Lys Arg Ser Leu Ala Met Lys Lys Gly Leu Pro Ile Leu Gly Val
305                 310                 315                 320

Phe Arg Ser Phe Ala Val Thr Gly Val Glu Pro Ser Val Met Gly Ile
                325                 330                 335

Gly Pro Ala Val Ala Ile Pro Ala Ala Thr Lys Leu Ala Gly Leu Asn
            340                 345                 350
```

```
Val Ser Asp Ile Asp Leu Phe Glu Ile Asn Glu Ala Phe Ala Ser Gln
            355                 360                 365

Tyr Val Tyr Ser Cys Lys Lys Leu Glu Leu Asp Met Glu Lys Val Asn
        370                 375                 380

Val Asn Gly Gly Ala Ile Ala Ile Gly His Pro Leu Gly Ala Thr Gly
385                 390                 395                 400

Ala Arg Cys Val Ala Thr Leu Leu His Glu Met Lys Arg Gly Lys
                405                 410                 415

Asp Cys Arg Phe Gly Val Ile Ser Met Cys Ile Gly Thr Gly Met Gly
                420                 425                 430

Ala Ala Ala Val Phe Glu Arg Gly Asp Ser Val Asp Asn Leu Ser Asn
                435                 440                 445

Ala Arg Val Ala Asn Gly Asp Ser His
450                 455

<210> SEQ ID NO 17
<211> LENGTH: 2270
<212> TYPE: DNA
<213> ORGANISM: Brassica sp.

<400> SEQUENCE: 17
gtgctcgagc aactactcag caattaaatc ggtagaggca cggcaccaaa agcatttggc        60
tctcttctct tttgttattt ttctggggaa aagttgtagg taatattgat aatcatggag       120
ggaattgatc acctagccga tgagaggaac aaggcggagt tcgatgtcga cgagatgaag       180
atcgtctggg ccggttctcg ccacgctttc gaggtttccg atcgaatcgc ccgcctcgtc       240
gccaccgatc cggtatccga aaaagcgat agagctaggt tgagcaggaa ggagctgttc        300
aagagcacgt tgaagaaatg tgctcacgct tggaagagga tcatcgagct tcgtctcacc       360
gaggaagaag caggaaggtt gaggttcttt gttgatcagc ctgcctttgt tgatcttcac       420
tggggaatgt ttgtgcctgc tatcaagggg cagggtacag aggagcagca agagaaatgg       480
ttgtctctgg ccaataagat gcagattatt ggtgttatg cacaaactga gcttggtcat        540
ggctctaatg ttcaaggact tgagacaacc gccacttttg atcccaagac ggatgagttt       600
gtgatccaca gcccaactca gacttcatcc aaatggtggc ctggtggctt gggaaaagtt       660
tctacccatg ctgttgttta cgctcgtctc atcactgacg gcaaagacta tggtgtccat       720
ggattcattg tgcaactgcg tagcttagaa gatcattctc ctcttccgaa ataaattgtt       780
ggtgatatcg ggacgaagat gggtaatgga gcatacaatt ctatggacaa cggttttctt       840
atgtttgatc aagttcgcat tcccagaaat caaatgctca tgaggctggc aaaagttaca       900
agggaaggaa aatatgttcc atcggatgtt ccaaagcagc taatgtatgg tactatggtg       960
tatgtgagac aaacaattgt ggcagatgct tcgaatgcac tatctagagc tgtttgcata      1020
gctacaaggt acagcgcagt acggaggcag tttggcgccc agaatggtgg cattgagact      1080
caggtgattg attataaaac tcagcaaaac aggctatttc ctttgttggc atcggcatat      1140
gcattccgat ttgtgggga gtggcttaaa tggctgtaca cggatgtaac tgcaagactg       1200
caggccagtg atttctcaac attgcctgag gctcatgcat gcactgcagg attgaaatct      1260
ctcaccacca cagccactgc ggacggcatt gaagaatgtc gtaagttatg tggtggacat      1320
ggttacttgt ggtgcagtgg gctccctgag ctgtttgctg tatatgttcc tgcctgtaca      1380
tatgaaggag acaacattgt gctacagttg caggttgcta gatttctcat gaagacagtg      1440
tcccagctgg gatctggaaa ggctcctgtt ggcacaactg cttatatggc tcgggcacaa      1500
```

-continued

```
catcttttgc aatgccgttc tggtgttcaa aaagctgagg attggttgaa ccctgctgcg    1560
gtagtggaag cttttgaagc aagggctctg agaatggccg ttgcttgtgc caaaaatctc    1620
agcaagtttg agaatcaaga acaaggattc tcagagctac tggccgagct ggttgaggcg    1680
gcaattgctc attgccaatt gattgttgtt ccaagttca tagctaagct agagcaagac     1740
ataggaggca aaggagtaaa gaaacagctg aacaatctgt gttacattta cgctctccat    1800
atccttcata aacacctcgg agatttcctc tcaaccaact ccatcactcc caaacaagcc    1860
tctctcgcca atgaccagct ccgttcctta tactcacagg tccgcc ctaa tgcggttgcg    1920 cttgtggacg ccttcaacta caccgaccat tacttgaact cggtgctagg acgttatgac    1980
ggtaatgtat acccgaagct ctttgaggaa gcatggaagg atccattgaa cgactcggtg    2040
gttcctgatg ggtaccagga atacattcga cccttgatca agcagcagct tcgtaccgcc    2100
aggctctgaa gagtttgctt tataacacat tcttcttctc ttttcagtat tattgtcttg    2160
aataaatttg ccggtttaaa aactggcgat acccttattt atgtgtagca aatgtaatgg    2220
ctgacacata cgtcggagtt ttagtactat ttttaaatta tagatctcgc              2270
```

<210> SEQ ID NO 18
<211> LENGTH: 664
<212> TYPE: PRT
<213> ORGANISM: Brassica sp.

<400> SEQUENCE: 18

```
Met Glu Gly Ile Asp His Leu Ala Asp Glu Arg Asn Lys Ala Glu Phe
  1               5                  10                  15

Asp Val Asp Glu Met Lys Ile Val Trp Ala Gly Ser Arg His Ala Phe
             20                  25                  30

Glu Val Ser Asp Arg Ile Ala Arg Leu Val Ala Thr Asp Pro Val Ser
         35                  40                  45

Glu Lys Ser Asp Arg Ala Arg Leu Ser Arg Lys Glu Leu Phe Lys Ser
     50                  55                  60

Thr Leu Lys Lys Cys Ala His Ala Trp Lys Arg Ile Ile Glu Leu Arg
 65                  70                  75                  80

Leu Thr Glu Glu Ala Gly Arg Leu Arg Phe Phe Val Asp Gln Pro
             85                  90                  95

Ala Phe Val Asp Leu His Trp Gly Met Phe Val Pro Ala Ile Lys Gly
            100                 105                 110

Gln Gly Thr Glu Glu Gln Gln Glu Lys Trp Leu Ser Leu Ala Asn Lys
        115                 120                 125

Met Gln Ile Ile Gly Cys Tyr Ala Gln Thr Glu Leu Gly His Gly Ser
    130                 135                 140

Asn Val Gln Gly Leu Glu Thr Thr Ala Thr Phe Asp Pro Lys Thr Asp
145                 150                 155                 160

Glu Phe Val Ile His Ser Pro Thr Gln Thr Ser Lys Trp Trp Pro
            165                 170                 175

Gly Gly Leu Gly Lys Val Ser Thr His Ala Val Tyr Ala Arg Leu
            180                 185                 190

Ile Thr Asp Gly Lys Asp Tyr Gly Val His Gly Phe Ile Val Gln Leu
        195                 200                 205

Arg Ser Leu Glu Asp His Ser Pro Leu Pro Asn Ile Ile Val Gly Asp
    210                 215                 220

Ile Gly Thr Lys Met Gly Asn Gly Ala Tyr Asn Ser Met Asp Asn Gly
225                 230                 235                 240
```

```
Phe Leu Met Phe Asp Gln Val Arg Ile Pro Arg Asn Gln Met Leu Met
                245                 250                 255

Arg Leu Ala Lys Val Thr Arg Glu Gly Lys Tyr Val Pro Ser Asp Val
            260                 265                 270

Pro Lys Gln Leu Met Tyr Gly Thr Met Val Tyr Val Arg Gln Thr Ile
        275                 280                 285

Val Ala Asp Ala Ser Asn Ala Leu Ser Arg Ala Val Cys Ile Ala Thr
    290                 295                 300

Arg Tyr Ser Ala Val Arg Arg Gln Phe Gly Ala Gln Asn Gly Gly Ile
305                 310                 315                 320

Glu Thr Gln Val Ile Asp Tyr Lys Thr Gln Gln Asn Arg Leu Phe Pro
                325                 330                 335

Leu Leu Ala Ser Ala Tyr Ala Phe Arg Phe Val Gly Glu Trp Leu Lys
            340                 345                 350

Trp Leu Tyr Thr Asp Val Thr Ala Arg Leu Gln Ala Ser Asp Phe Ser
        355                 360                 365

Thr Leu Pro Glu Ala His Ala Cys Thr Ala Gly Leu Lys Ser Leu Thr
    370                 375                 380

Thr Thr Ala Thr Ala Asp Gly Ile Glu Glu Cys Arg Lys Leu Cys Gly
385                 390                 395                 400

Gly His Gly Tyr Leu Trp Cys Ser Gly Leu Pro Glu Leu Phe Ala Val
                405                 410                 415

Tyr Val Pro Ala Cys Thr Tyr Glu Gly Asp Asn Ile Val Leu Gln Leu
            420                 425                 430

Gln Val Ala Arg Phe Leu Met Lys Thr Val Ser Gln Leu Gly Ser Gly
        435                 440                 445

Lys Ala Pro Val Gly Thr Thr Ala Tyr Met Ala Arg Ala Gln His Leu
    450                 455                 460

Leu Gln Cys Arg Ser Gly Val Gln Lys Ala Glu Asp Trp Leu Asn Pro
465                 470                 475                 480

Ala Ala Val Val Glu Ala Phe Glu Ala Arg Ala Leu Arg Met Ala Val
                485                 490                 495

Ala Cys Ala Lys Asn Leu Ser Lys Phe Glu Asn Gln Glu Gln Gly Phe
            500                 505                 510

Ser Glu Leu Leu Ala Glu Leu Val Glu Ala Ile Ala His Cys Gln
        515                 520                 525

Leu Ile Val Ser Lys Phe Ile Ala Lys Leu Glu Gln Asp Ile Gly
    530                 535                 540

Gly Lys Gly Val Lys Lys Gln Leu Asn Asn Leu Cys Tyr Ile Tyr Ala
545                 550                 555                 560

Leu His Ile Leu His Lys His Leu Gly Asp Phe Leu Ser Thr Asn Ser
                565                 570                 575

Ile Thr Pro Lys Gln Ala Ser Leu Ala Asn Asp Gln Leu Arg Ser Leu
            580                 585                 590

Tyr Ser Gln Val Arg Pro Asn Ala Val Ala Leu Val Asp Ala Phe Asn
        595                 600                 605

Tyr Thr Asp His Tyr Leu Asn Ser Val Leu Gly Arg Tyr Asp Gly Asn
    610                 615                 620

Val Tyr Pro Lys Leu Phe Glu Glu Ala Trp Lys Asp Pro Leu Asn Asp
625                 630                 635                 640

Ser Val Val Pro Asp Gly Tyr Gln Glu Tyr Ile Arg Pro Leu Ile Lys
                645                 650                 655
```

Gln Gln Leu Arg Thr Ala Arg Leu
          660

<210> SEQ ID NO 19
<211> LENGTH: 2297
<212> TYPE: DNA
<213> ORGANISM: Brassica sp.

<400> SEQUENCE: 19

| | | | | |
|---|---|---|---|---|
| gcgggatcca gatttcgttt tttaatttat ttaccataat tcaactaatt gaacggtctc | 60 |
| ctcttcatct tcatctcctc caccgtttcg aaaatcttca tttgatattt tctttctcta | 120 |
| atggcgttgg aagagttttc cgagatagct gcggcgagga ggattcagag actgtcgtca | 180 |
| catatctctc ccgctttaac ggagccgccg cagctgcaga cggaggcgtg ctcttcgcgg | 240 |
| acgaggaagc tggtggtcaa cggtcaggcg ttgtctctct acatgaaggg gaagcacagg | 300 |
| gatattcagg agaaagtgca cgagttctac aactctcgtc ccgatttgca gacgccgctc | 360 |
| gagatctcca aggacgatca tcgagagttg tgtatgaggc agctatatgc gcttgtgaga | 420 |
| gaagctggta taaggccgtt taggtatgtg gctgatgatc cggccaagta ttttgcgatc | 480 |
| atggaagctg ttgggagtgt ggatatgtcg tttgggatca agatgggtgt tcaatacagt | 540 |
| ctttggggag gctctgtgat caacttggga acaaagaagc atagagacaa gtatttcgat | 600 |
| ggcattgaca atctagacta cctcggttgc tttgctatga ctgaactcca ccatggttca | 660 |
| aatgttcaag gtctccagac cacggccaca tttgatccca tcacagacga gttcataatc | 720 |
| gacacaccac acgatggagc catcaaatgg tggataggaa acgccgcagt tcacggaaaa | 780 |
| ttcgccacag ttttcgccag gctcatcctt ccaacgcacg acaccaaagg agtctcagac | 840 |
| atgggcgttc acgccttcat agtccccata agagacatga aaacacacca gaccctccca | 900 |
| ggcgtcgaga ttcaagactg cggacagaaa gtaggtctga acggagtcga caacggggct | 960 |
| ttgcggttcc gttccgtgag aatcccacgt gacaatctcc tcaaccgctt cggagatgtg | 1020 |
| tcacgagacg gcaagtacac aagcagctta ccaacgatca acaaaagatt cggtgcaaca | 1080 |
| ctcggtgagc ttgtaggtgg acgagtggct cttgcttact catccgttgg tgtactcaaa | 1140 |
| gtctcggcca ctattgctat acgttactcg ttgttaagac aacagtttgg tcctccgaag | 1200 |
| caaccagagg ttagtattct tgattaccag tctcaacaac acaagttaat gcccatgttg | 1260 |
| gcttctacct atgcgtacca tttcgcaact gtgtacctcg tggagaaata ttcggagatg | 1320 |
| aagaagacta cgatgagca gttagttgct gatgtccatg cgctatctgc tggtctcaag | 1380 |
| tcttatataa cgtcttacac ggctaagtcg ctctcggtct gtagagaagc ttgtggagga | 1440 |
| catggttacg cagctgttaa caggtttgga ggcttgagga tgatcatga tatattccaa | 1500 |
| acatttgaag gagacaacac agtgcttcta caacaggtgg cagctgattt gctgaagaga | 1560 |
| tataaagaga agttccaagg tgggacattg acagtcacat ggagttactt gagagaatcg | 1620 |
| atgagctctt atttggctca gccaaatcca gttacagctc gttgggaggg tgaagatcat | 1680 |
| ctaagagatc ctaagttcca actagatgct ttccggtatc gaacatcacg tctcctacaa | 1740 |
| agtgtggcaa tgcgtttgaa gaaacacagc aagacacttg gaacattcgg tgcatggaac | 1800 |
| agatgcttga accatctctt gacactagca gaatctcaca ttgaaacagt cattctcgcc | 1860 |
| aagttcattg aagctgttag aaagtgtccg gacccaagtg caagagctgg tctgaaacta | 1920 |
| gtatgtgatc tttacgcatt ggaccgaata tggaatgata taggaacgta ccgtaacgtg | 1980 |
| gactatgtgg cgcctaacaa agccaaggcg attcataagt tggctgagta tttgagtttc | 2040 |

-continued

```
caagtaagga acgtggccaa ggagctagtg gacgcgttcg agctgcctga tcacgttact    2100
cgagcgccga ttgctatgca agctgatgct tattcacagt atactcaagt gttggattc    2160 tgaaaatgtt gaaacgaata aatatattta tgtctcaaga ttgaagatga tctcaagttt    2220
ggaatatgtt atatagttac aatgtattaa acacagagtt aagagaataa acagaggaat    2280
attctgttgg atcctcg                                                   2297
```

<210> SEQ ID NO 20
<211> LENGTH: 680
<212> TYPE: PRT
<213> ORGANISM: Brassica sp.

<400> SEQUENCE: 20

```
Met Ala Leu Glu Glu Phe Ser Glu Ile Ala Ala Arg Arg Ile Gln
  1               5                  10                  15

Arg Leu Ser Ser His Ile Ser Pro Ala Leu Thr Glu Pro Pro Gln Leu
             20                  25                  30

Gln Thr Glu Ala Cys Ser Ser Arg Thr Arg Lys Leu Val Val Asn Gly
         35                  40                  45

Gln Ala Leu Ser Leu Tyr Met Lys Gly Lys His Arg Asp Ile Gln Glu
     50                  55                  60

Lys Val His Glu Phe Tyr Asn Ser Arg Pro Asp Leu Gln Thr Pro Leu
 65                  70                  75                  80

Glu Ile Ser Lys Asp Asp His Arg Glu Leu Cys Met Arg Gln Leu Tyr
                 85                  90                  95

Ala Leu Val Arg Glu Ala Gly Ile Arg Pro Phe Arg Tyr Val Ala Asp
            100                 105                 110

Asp Pro Ala Lys Tyr Phe Ala Ile Met Glu Ala Val Gly Ser Val Asp
        115                 120                 125

Met Ser Phe Gly Ile Lys Met Gly Val Gln Tyr Ser Leu Trp Gly Gly
    130                 135                 140

Ser Val Ile Asn Leu Gly Thr Lys Lys His Arg Asp Lys Tyr Phe Asp
145                 150                 155                 160

Gly Ile Asp Asn Leu Asp Tyr Leu Gly Cys Phe Ala Met Thr Glu Leu
                165                 170                 175

His His Gly Ser Asn Val Gln Gly Leu Gln Thr Ala Thr Phe Asp
            180                 185                 190

Pro Ile Thr Asp Glu Phe Ile Ile Asp Thr Pro His Asp Gly Ala Ile
        195                 200                 205

Lys Trp Trp Ile Gly Asn Ala Ala Val His Gly Lys Phe Ala Thr Val
    210                 215                 220

Phe Ala Arg Leu Ile Leu Pro Thr His Asp Thr Lys Gly Val Ser Asp
225                 230                 235                 240

Met Gly Val His Ala Phe Ile Val Pro Ile Arg Asp Met Lys Thr His
                245                 250                 255

Gln Thr Leu Pro Gly Val Glu Ile Gln Asp Cys Gly Gln Lys Val Gly
            260                 265                 270

Leu Asn Gly Val Asp Asn Gly Ala Leu Arg Phe Arg Ser Val Arg Ile
        275                 280                 285

Pro Arg Asp Asn Leu Leu Asn Arg Phe Gly Asp Val Ser Arg Asp Gly
    290                 295                 300

Lys Tyr Thr Ser Ser Leu Pro Thr Ile Asn Lys Arg Phe Gly Ala Thr
305                 310                 315                 320

Leu Gly Glu Leu Val Gly Gly Arg Val Ala Leu Ala Tyr Ser Ser Val
```

-continued

```
              325                 330                 335
Gly Val Leu Lys Val Ser Ala Thr Ile Ala Ile Arg Tyr Ser Leu Leu
                    340                 345                 350
Arg Gln Gln Phe Gly Pro Lys Gln Pro Glu Val Ser Ile Leu Asp
                355                 360                 365
Tyr Gln Ser Gln Gln His Lys Leu Met Pro Met Leu Ala Ser Thr Tyr
    370                 375                 380
Ala Tyr His Phe Ala Thr Val Tyr Leu Val Glu Lys Tyr Ser Glu Met
385                 390                 395                 400
Lys Lys Thr Asn Asp Glu Gln Leu Val Ala Asp Val His Ala Leu Ser
                405                 410                 415
Ala Gly Leu Lys Ser Tyr Ile Thr Ser Tyr Thr Ala Lys Ser Leu Ser
                420                 425                 430
Val Cys Arg Glu Ala Cys Gly Gly His Gly Tyr Ala Ala Val Asn Arg
                435                 440                 445
Phe Gly Gly Leu Arg Asn Asp His Asp Ile Phe Gln Thr Phe Glu Gly
    450                 455                 460
Asp Asn Thr Val Leu Leu Gln Gln Val Ala Ala Asp Leu Leu Lys Arg
465                 470                 475                 480
Tyr Lys Glu Lys Phe Gln Gly Gly Thr Leu Thr Val Thr Trp Ser Tyr
                485                 490                 495
Leu Arg Glu Ser Met Ser Ser Tyr Leu Ala Gln Pro Asn Pro Val Thr
                500                 505                 510
Ala Arg Trp Glu Gly Glu Asp His Leu Arg Asp Pro Lys Phe Gln Leu
                515                 520                 525
Asp Ala Phe Arg Tyr Arg Thr Ser Arg Leu Leu Gln Ser Val Ala Met
    530                 535                 540
Arg Leu Lys Lys His Ser Lys Thr Leu Gly Thr Phe Gly Ala Trp Asn
545                 550                 555                 560
Arg Cys Leu Asn His Leu Leu Thr Leu Ala Glu Ser His Ile Glu Thr
                565                 570                 575
Val Ile Leu Ala Lys Phe Ile Glu Ala Val Arg Lys Cys Pro Asp Pro
                580                 585                 590
Ser Ala Arg Ala Gly Leu Lys Leu Val Cys Asp Leu Tyr Ala Leu Asp
                595                 600                 605
Arg Ile Trp Asn Asp Ile Gly Thr Tyr Arg Asn Val Asp Tyr Val Ala
    610                 615                 620
Pro Asn Lys Ala Lys Ala Ile His Lys Leu Ala Glu Tyr Leu Ser Phe
625                 630                 635                 640
Gln Val Arg Asn Val Ala Lys Glu Leu Val Asp Ala Phe Glu Leu Pro
                645                 650                 655
Asp His Val Thr Arg Ala Pro Ile Ala Met Gln Ala Asp Ala Tyr Ser
                660                 665                 670
Gln Tyr Thr Gln Val Val Gly Phe
    675                 680
```

<210> SEQ ID NO 21
<211> LENGTH: 1675
<212> TYPE: DNA
<213> ORGANISM: Brassica sp.

<400> SEQUENCE: 21
gtgagatctc catcctaata cgactcacta tagggctcga gggccgcccg ggcaggtccg      60
agtttgaatc gggataaaaa tggagaaagc tatcgagaga caaagagttc ttcttgaaca     120

-continued

```
tctccgtcct tcttcttctt cctcccacag tttcgagggc tctctctctg cttctgcttg      180
cttggctggg gacagtgctg cttatcaaag gacctctctc tatggagatg atgttgtcat      240
tgtcgcggca cataggactg cactttgcaa gtccaaacgt ggcaacttca aggatactta      300
ccctgatgat cttcttgcac ctgttttgag ggctttgata gagaagacaa atctagaccc      360
aagtgaagtt ggtgacattg ttgttggtac tgttttggca cctggttctc agagagccag      420
cgaatgcagg atgtctgctt tctatgctgg tttccctgaa accgtggcgg tgaggaccgt      480
gaatagacag tgctcctctg ggcttcaggc tgttgctgac gttgccgctg ccatcaaagc      540
tggattttat gatattggta ttggggctgg attggagtcc atgactacca acccaatggc      600
atgggaaggg tcagtcaacc cagcggtgaa gaagtttgag caagcacaga attgtcttct      660
ccctatgggt gttacttccg aaaatgtagc acaccgcttt ggtgtctcaa ggcaggagca      720
agatcaggct gctgttgact cgcacaggaa ggcagctgct gctactgctg ctggtaagtt      780
caaggatgag atcattccag ttaaaaccaa gcttgttgac ccaaagacag gagatgagaa      840
acccattaca gtctctgttg atgatgggat ccgaccaagc acaacccttg ctactcttgg      900
gaagctgaag ccagtgttta aaaggatgg aaccacaaca gctggaaact ccagccaagt      960
tagtgatggt gctggagcgg ttctcctcat gaggagaagt gttgctactc agaaaggact      1020
tcccgttctt ggtgtattca ggacatttgc tgcagttggt gttgacccag caatcatggg      1080
tgtcggtcca gcagttgcta ttcctgctgc agttaaagct gctggtttag aactcgatga      1140
catcgacttg tttgagatca acgaggcatt tgcatctcag tttgttattg ccgtaacaag      1200
ttgggacttg cgcagagaaa atcaatgtca acggaggcgc aatggccata ggacatcctt      1260
tgggtgctac aggagccgtt gcgttgctac tttgttgcac gagatgaaac gccgtggaaa      1320
aaactgtcga tttgggggtag tgtcaatgtg cattgggacg ggatgggtgc aacggcagtg      1380
tttgagagag gagatgaagt tgatgagctc cgcaacgcaa ggaaagttga atcgcatggc      1440
cttttgtcca aggacgctcg ttagaaatat tatgatgatg tgtcaatcac caagaaaacc      1500
ctcttcactt ttttcccagc ttttttcagt tttattatac ttgtttgaat aaagcagctc      1560
agcgaatgtt tgccggagtc ttttttatat tcttcttgac atggtcatgt gtttagtagt      1620
atatttttat ttacgcgtgt gattttctat aatattgttc ttctcggtcg actgc         1675
```

<210> SEQ ID NO 22
<211> LENGTH: 490
<212> TYPE: PRT
<213> ORGANISM: Brassica sp.

<400> SEQUENCE: 22

```
Met Glu Lys Ala Ile Glu Arg Gln Arg Val Leu Leu Glu His Leu Arg
  1               5                  10                  15

Pro Ser Ser Ser Ser His Ser Phe Glu Gly Ser Leu Ser Ala Ser
                 20                  25                  30

Ala Cys Leu Ala Gly Asp Ser Ala Ala Tyr Gln Arg Thr Ser Leu Tyr
             35                  40                  45

Gly Asp Asp Val Val Ile Val Ala Ala His Arg Thr Ala Leu Cys Lys
         50                  55                  60

Ser Lys Arg Gly Asn Phe Lys Asp Thr Tyr Pro Asp Asp Leu Leu Ala
 65                  70                  75                  80

Pro Val Leu Arg Ala Leu Ile Glu Lys Thr Asn Leu Asp Pro Ser Glu
                 85                  90                  95
```

```
Val Gly Asp Ile Val Val Gly Thr Val Leu Ala Pro Gly Ser Gln Arg
            100                 105                 110

Ala Ser Glu Cys Arg Met Ser Ala Phe Tyr Ala Gly Phe Pro Glu Thr
        115                 120                 125

Val Ala Val Arg Thr Val Asn Arg Gln Cys Ser Ser Gly Leu Gln Ala
    130                 135                 140

Val Ala Asp Val Ala Ala Ile Lys Ala Gly Phe Tyr Asp Ile Gly
145                 150                 155                 160

Ile Gly Ala Gly Leu Glu Ser Met Thr Thr Asn Pro Met Ala Trp Glu
                165                 170                 175

Gly Ser Val Asn Pro Ala Val Lys Lys Phe Glu Gln Ala Gln Asn Cys
            180                 185                 190

Leu Leu Pro Met Gly Val Thr Ser Glu Asn Val Ala His Arg Phe Gly
        195                 200                 205

Val Ser Arg Gln Glu Gln Asp Gln Ala Ala Val Asp Ser His Arg Lys
    210                 215                 220

Ala Ala Ala Ala Thr Ala Ala Gly Lys Phe Lys Asp Glu Ile Ile Pro
225                 230                 235                 240

Val Lys Thr Lys Leu Val Asp Pro Lys Thr Gly Asp Glu Lys Pro Ile
                245                 250                 255

Thr Val Ser Val Asp Asp Gly Ile Arg Pro Ser Thr Thr Leu Ala Thr
            260                 265                 270

Leu Gly Lys Leu Lys Pro Val Phe Lys Lys Asp Gly Thr Thr Thr Ala
        275                 280                 285

Gly Asn Ser Ser Gln Val Ser Asp Gly Ala Gly Ala Val Leu Leu Met
    290                 295                 300

Arg Arg Ser Val Ala Thr Gln Lys Gly Leu Pro Val Leu Gly Val Phe
305                 310                 315                 320

Arg Thr Phe Ala Ala Val Gly Val Asp Pro Ala Ile Met Gly Val Gly
                325                 330                 335

Pro Ala Val Ala Ile Pro Ala Ala Val Lys Ala Ala Gly Leu Glu Leu
            340                 345                 350

Asp Asp Ile Asp Leu Phe Glu Ile Asn Glu Ala Phe Ala Ser Gln Phe
        355                 360                 365

Val Ile Ala Val Thr Ser Trp Asp Leu Arg Arg Glu Asn Gln Cys Gln
    370                 375                 380

Arg Arg Arg Asn Gly His Arg Thr Ser Phe Gly Cys Tyr Arg Ser Arg
385                 390                 395                 400

Cys Val Ala Thr Leu Leu His Glu Met Lys Arg Arg Gly Lys Asn Cys
                405                 410                 415

Arg Phe Gly Val Val Ser Met Cys Ile Gly Thr Gly Trp Val Gln Arg
            420                 425                 430

Gln Cys Leu Arg Glu Glu Met Lys Leu Met Ser Ser Ala Thr Gln Gly
        435                 440                 445

Lys Leu Asn Arg Met Ala Phe Cys Pro Arg Thr Leu Val Arg Asn Ile
    450                 455                 460

Met Met Met Cys Gln Ser Pro Arg Lys Pro Ser Ser Leu Phe Ser Gln
465                 470                 475                 480

Leu Phe Ser Val Leu Leu Tyr Leu Phe Glu
                485                 490

<210> SEQ ID NO 23
<211> LENGTH: 1665
<212> TYPE: DNA
```

<213> ORGANISM: Brassica sp.

<400> SEQUENCE: 23

| | | | | | |
|---|---|---|---|---|---|
| cctctaatac | gactcactat | agggaaagct | ggtacgcctg | caggtaccgg | tccggaattc | 60 |
| ccgggtcgac | ccacgcgtcc | gacgtccggc | tgtgaactgt | gctgctgagc | tttccccaat | 120 |
| ggctgctttt | ggagacgacg | ttgtgatcgt | tgcggcgtac | cgcactgcca | tttgtaaagc | 180 |
| taagcgtgga | gggttcaaag | atactctccc | agatgatctt | ctcgcttctg | ttctcaaggc | 240 |
| tgtggtggaa | aggacgtctt | tggatccaag | tgaagttggg | gatattgttg | ttggtaccgt | 300 |
| tatagctcct | ggctctcaga | gggccatgga | gtgtagagta | gctgcattct | tgctggctt | 360 |
| tcctgactct | gtgccgatta | gaactgtcaa | cagacaatgc | tcatcaggac | tacaagcagt | 420 |
| tgctgatgtt | gctgcttcca | tcagagctgg | atattacgac | attggtattg | gtgctggagt | 480 |
| ggagtcaatg | tcaactgatc | atattcctgg | aggcggattt | aacaccacaa | acccgagggc | 540 |
| acaagagttt | cctggagctc | gtgactgctt | gcttccaatg | ggcattacct | ctgaaaacgt | 600 |
| tgcagagaga | tacggtgtca | agagaagaa | gcaagacatg | gctgcggtgg | agtctcacaa | 660 |
| gcgtgctgca | gctgcaaacg | cctctggtaa | actcaaggac | gagatagttc | ctgttgctac | 720 |
| taagattgtt | gacccggtga | caaaagcaga | gaagccaatc | gttgtttctg | ttgatgatgg | 780 |
| tgtacgtcca | aactcaaaca | tggctgatct | ggcaaagctg | aagacagtct | ttaaacctaa | 840 |
| tggttcaacc | acagcaggta | atgctagtca | gattagtgat | ggtgctggag | ctgtactgct | 900 |
| aatgaagagg | agcttggcca | tgaagaaggg | acttcccatt | cttggagttt | tcaggagctt | 960 |
| tgctgttact | ggtgtggatc | cggctgtaat | gggtatcggt | ccagcttacg | ccattcccgc | 1020 |
| tgcagccaac | cttgcaggac | tcaaagttag | cgatatcgat | ctatttgaga | tcaatgaggc | 1080 |
| atttgcatct | cagtatgtgt | actgttgcaa | gaagctggag | ctggatgtgg | aaaaggtcaa | 1140 |
| tgttaatgga | ggagccattg | ctattggcca | tcctcttggt | gctacaggag | ctcgatgtgt | 1200 |
| tgcgacattg | ttgcatgaga | tgaaacggag | agggaaagac | tgccgctttg | gagtgatttc | 1260 |
| aatgtgcata | ggcactggta | tgggagctgc | agctgtgttt | gagagaggag | actctgttga | 1320 |
| tgacctgtcc | aatgcccgtg | tggtggctaa | tgggagcggt | cattagaaca | aggttggaat | 1380 |
| aaggagaagc | aatgaaagca | ttaagtcaaa | taaaaaagtg | tgaagcttaa | gctcttcac | 1440 |
| aacaatttgt | aattctgaat | ttaaaatgta | tcaactagta | cttgtgtgtg | aacaaagagt | 1500 |
| caaatgctaa | aaaccaaagt | tacatctttc | ctcctaaaaa | aaaaaaaaa | aaaaaccaaa | 1560 |
| aaaaaaaaa | aaaggcggcc | gctctagagg | atccaagctt | acgtacgcgg | catgcgacgt | 1620 |
| catagctctt | ctatagtgtc | acctaaattc | aattcactgg | ccgtg | | 1665 |

<210> SEQ ID NO 24
<211> LENGTH: 427
<212> TYPE: PRT
<213> ORGANISM: Brassica sp.

<400> SEQUENCE: 24

Arg Pro Ala Val Asn Cys Ala Ala Glu Leu Ser Pro Met Ala Ala Phe
1               5                   10                  15

Gly Asp Asp Val Val Ile Val Ala Ala Tyr Arg Thr Ala Ile Cys Lys
            20                  25                  30

Ala Lys Arg Gly Gly Phe Lys Asp Thr Leu Pro Asp Asp Leu Leu Ala
        35                  40                  45

Ser Val Leu Lys Ala Val Val Glu Arg Thr Ser Leu Asp Pro Ser Glu
    50                  55                  60

-continued

Val Gly Asp Ile Val Val Gly Thr Val Ile Ala Pro Gly Ser Gln Arg
 65                  70                  75                  80

Ala Met Glu Cys Arg Val Ala Ala Phe Phe Ala Gly Phe Pro Asp Ser
                 85                  90                  95

Val Pro Ile Arg Thr Val Asn Arg Gln Cys Ser Ser Gly Leu Gln Ala
            100                 105                 110

Val Ala Asp Val Ala Ala Ser Ile Arg Ala Gly Tyr Tyr Asp Ile Gly
        115                 120                 125

Ile Gly Ala Gly Val Glu Ser Met Ser Thr Asp His Ile Pro Gly Gly
    130                 135                 140

Gly Phe Asn Thr Thr Asn Pro Arg Ala Gln Glu Phe Pro Gly Ala Arg
145                 150                 155                 160

Asp Cys Leu Leu Pro Met Gly Ile Thr Ser Glu Asn Val Ala Glu Arg
                165                 170                 175

Tyr Gly Val Thr Arg Glu Glu Gln Asp Met Ala Ala Val Glu Ser His
            180                 185                 190

Lys Arg Ala Ala Ala Asn Ala Ser Gly Lys Leu Lys Asp Glu Ile
        195                 200                 205

Val Pro Val Ala Thr Lys Ile Val Asp Pro Val Thr Lys Ala Glu Lys
    210                 215                 220

Pro Ile Val Val Ser Val Asp Asp Gly Val Arg Pro Asn Ser Asn Met
225                 230                 235                 240

Ala Asp Leu Ala Lys Leu Lys Thr Val Phe Lys Pro Asn Gly Ser Thr
                245                 250                 255

Thr Ala Gly Asn Ala Ser Gln Ile Ser Asp Gly Ala Gly Ala Val Leu
            260                 265                 270

Leu Met Lys Arg Ser Leu Ala Met Lys Lys Gly Leu Pro Ile Leu Gly
        275                 280                 285

Val Phe Arg Ser Phe Ala Val Thr Gly Val Asp Pro Ala Val Met Gly
    290                 295                 300

Ile Gly Pro Ala Tyr Ala Ile Pro Ala Ala Asn Leu Ala Gly Leu Leu
305                 310                 315                 320

Lys Val Ser Asp Ile Asp Leu Phe Glu Ile Asn Glu Ala Phe Ala Ser
                325                 330                 335

Gln Tyr Val Tyr Cys Cys Lys Lys Leu Glu Leu Asp Val Glu Lys Val
            340                 345                 350

Asn Val Asn Gly Gly Ala Ile Ala Ile Gly His Pro Leu Gly Ala Thr
        355                 360                 365

Gly Ala Arg Cys Val Ala Thr Leu Leu His Glu Met Lys Arg Arg Gly
370                 375                 380

Lys Asp Cys Arg Phe Gly Val Ile Ser Met Cys Ile Gly Thr Gly Met
385                 390                 395                 400

Gly Ala Ala Ala Val Phe Glu Arg Gly Asp Ser Val Asp Asp Leu Ser
                405                 410                 415

Asn Ala Arg Val Val Ala Asn Gly Ser Gly His
            420                 425

<210> SEQ ID NO 25
<211> LENGTH: 56
<212> TYPE: DNA
<213> ORGANISM: Artificial Sequence
<220> FEATURE:
<223> OTHER INFORMATION: Synthetic oligonucleotide

<400> SEQUENCE: 25
cgcgatttaa atggcgcgcc ctgcaggcgg ccgcctgcag ggcgcgccat ttaaat        56

<210> SEQ ID NO 26
<211> LENGTH: 1638
<212> TYPE: DNA
<213> ORGANISM: Brassica sp.

<400> SEQUENCE: 26
gccctctaga tgcatgctcg agcggcccgc cagtgtgatg gatatctgca gaattcgccc        60
ttccatccta atacgactca ctatagggct cgaggcggcc gcccgggcag gtcgaaccca       120
aagaaacgtt ttccatcgca atcgtcgcca ccatgactgt gctatcatca tctacagatc       180
gagatgaggc tgagaagaag gtgaagagtt cgtatatcga tttgccggct atggacgtat       240
ccgttgcatt tcctcaagca accccagctt ctaagttccc accttgcact tcagactatt       300
accatttcaa tgaactgttg actccggagg agcaggctgt gcggaagaga gtgagggagt       360
tcatggagaa agaagttgct ccgattatga cagagtactg ggagaaggca gagtttccat       420
tccatatcat tccaaagctt ggagctttag gtattgttgg tggctctatt aagggttatg       480
gctgtcctgg cctctccatc acagccaacg ccatttcaac agcagagata tctagagttg       540
atgcaagctg tgggactttt aatttggtgc atacctcttt gggcatgctc actattgcac       600
tttgtggatc agaagaacag aagcacaagt atttgccttc tttggctcag atgaaaactg       660
tgacttgttg ggcttttgaca gaacctgaca atggaagtga tgcaagtgct ctacaaacaa       720
ctgccacaaa ggttgaagga ggttgggtac ttacgggaca aaagcgttgg atcggtaaca       780
gcacctttc agatctgttg atcatccttg ctaggaatac gacaactaac caagtgaatg       840
gattcatagt caagaaagat gcgcctggct aacggttac taagatccca aataaaatag       900
gtttacgtat tgttcaaaat ggagatattc tactacagaa tgtctttgtt cctgatgagg       960
agcggttacc tggactaaat tcttttcaag acacaagcaa ggtccttgct gtctcacgtg      1020
taatggtggc ctggcaacca attggtgtat caatgggagt ctacgacatg tgtcacaggt      1080
atctaaagga gaggaaacag tttggagcac cgttggctac attccagata aaccaacaga      1140
agcttgtgaa gatgctgggc aatgttcaag caatgtttat gatgggttgg cgcctctgca      1200
agctatatga gtcgggtcag atgactccag gtcaagccag tttaggaaag gcatggatct      1260
catccaaggc aagggaagct gcttctttag gtcgggagtt acttggtggg aatggagttg      1320
taggggatt tctggtggca aaggctttcg gtgaccttga acccattttt acatacgaag      1380
ggacgtacga cataaacacc ttagtgacgg ggagggaagt taccaggatt gcgagtttca      1440
aaccccagc ttcacggggc cgtagccgtc tttaaggttg tgcagtgttt gttgttgttg      1500
gctgttagtt actttggtaa aatgtaatgt gtgagcttta catttacctg gagacactaa      1560
atgcgccaaa taatattggc ataaagggac atatgcaacc attgtattgc aataaaggat      1620
ccgtgctgtg taccggtt                                                   1638

<210> SEQ ID NO 27
<211> LENGTH: 440
<212> TYPE: PRT
<213> ORGANISM: Brassica sp.

<400> SEQUENCE: 27

Met Thr Val Leu Ser Ser Ser Thr Asp Arg Asp Glu Ala Glu Lys Lys
 1               5                  10                  15

Val Lys Ser Ser Tyr Ile Asp Leu Pro Ala Met Asp Val Ser Val Ala

```
                20                  25                  30
Phe Pro Gln Ala Thr Pro Ala Ser Lys Phe Pro Cys Thr Ser Asp
            35                  40                  45
Tyr Tyr His Phe Asn Glu Leu Leu Thr Pro Glu Gln Ala Val Arg
 50                  55                  60
Lys Arg Val Arg Glu Phe Met Glu Lys Glu Val Ala Pro Ile Met Thr
 65                  70                  75                  80
Glu Tyr Trp Glu Lys Ala Glu Phe Pro Phe His Ile Ile Pro Lys Leu
                85                  90                  95
Gly Ala Leu Gly Ile Val Gly Gly Ser Ile Lys Gly Tyr Gly Cys Pro
                100                 105                 110
Gly Leu Ser Ile Thr Ala Asn Ala Ile Ser Thr Ala Glu Ile Ser Arg
            115                 120                 125
Val Asp Ala Ser Cys Gly Thr Phe Asn Leu Val His Thr Ser Leu Gly
 130                 135                 140
Met Leu Thr Ile Ala Leu Cys Gly Ser Glu Glu Gln Lys His Lys Tyr
 145                 150                 155                 160
Leu Pro Ser Leu Ala Gln Met Lys Thr Val Thr Cys Trp Ala Leu Thr
                165                 170                 175
Glu Pro Asp Asn Gly Ser Asp Ala Ser Ala Leu Gln Thr Thr Ala Thr
                180                 185                 190
Lys Val Glu Gly Gly Trp Val Leu Thr Gly Gln Lys Arg Trp Ile Gly
            195                 200                 205
Asn Ser Thr Phe Ser Asp Leu Leu Ile Ile Leu Ala Arg Asn Thr Thr
 210                 215                 220
Thr Asn Gln Val Asn Gly Phe Ile Val Lys Lys Asp Ala Pro Gly Leu
 225                 230                 235                 240
Thr Val Thr Lys Ile Pro Asn Lys Ile Gly Leu Arg Ile Val Gln Asn
                245                 250                 255
Gly Asp Ile Leu Leu Gln Asn Val Phe Val Pro Asp Glu Glu Arg Leu
                260                 265                 270
Pro Gly Leu Asn Ser Phe Gln Asp Thr Ser Lys Val Leu Ala Val Ser
            275                 280                 285
Arg Val Met Val Ala Trp Gln Pro Ile Gly Val Ser Met Gly Val Tyr
 290                 295                 300
Asp Met Cys His Arg Tyr Leu Lys Glu Arg Lys Gln Phe Gly Ala Pro
 305                 310                 315                 320
Leu Ala Thr Phe Gln Ile Asn Gln Gln Lys Leu Val Lys Met Leu Gly
                325                 330                 335
Asn Val Gln Ala Met Phe Met Met Gly Trp Arg Leu Cys Lys Leu Tyr
                340                 345                 350
Glu Ser Gly Gln Met Thr Pro Gly Gln Ala Ser Leu Gly Lys Ala Trp
            355                 360                 365
Ile Ser Ser Lys Ala Arg Glu Ala Ala Ser Leu Gly Arg Glu Leu Leu
 370                 375                 380
Gly Gly Asn Gly Val Val Gly Asp Phe Leu Val Ala Lys Ala Phe Gly
 385                 390                 395                 400
Asp Leu Glu Pro Ile Phe Thr Tyr Glu Gly Thr Tyr Asp Ile Asn Thr
                405                 410                 415
```

-continued

```
Leu Val Thr Gly Arg Glu Val Thr Arg Ile Ala Ser Phe Lys Pro Pro
            420                 425                 430

Ala Ser Arg Gly Arg Ser Arg Leu
            435             440
```

US 6,489,461 B1

NUCLEIC ACID SEQUENCES ENCODING PROTEINS INVOLVED IN FATTY ACID BETA-OXIDATION AND METHODS OF USE

This application claims the benefit of U.S. Provisional Application No. 60/138,162 filed Jun. 8, 1999.

TECHNICAL FIELD

The present invention is directed to nucleic acid and amino acid sequences and constructs, and methods related thereto.

BACKGROUND

Fatty acids are organic acids having a hydrocarbon chain of from about 4 to 24 carbons. Many different kinds of fatty acids are known which differ from each other in chain length, and in the presence, number and position of double bonds. In cells, fatty acids typically exist in covalently bound forms, the carboxyl portion being referred to as a fatty acyl group. The chain length and degree of saturation of these molecules is often depicted by the formula CX:Y, where "X" indicates number of carbons and "Y" indicates number of double bands. As the carbon chain of fatty acyl molecules always contains an even number of carbons, the formula "$C_{2X}$" may also be used to represent carbon chain length.

Fatty acyl groups are major components of many lipids, and their long, non-polar hydrocarbon chain is responsible for the water-insoluble nature of these lipid molecules. The type of covalent linkage of the fatty acyl group to other factors can vary. For example, in biosynthetic reactions they may be covalently bound via a thioester linkage to an acyl carrier protein (ACP) or to CoenzymeA (CoA), depending on the particular enzymatic reaction. In waxes, fatty acyl groups are linked to fatty alcohols via an ester linkage, and triacylglycerols have three fatty acyl groups linked to a glycerol molecule via an ester linkage.

The fatty acid composition of an oil determines its physical and chemical properties, and thus its uses. Plants, especially plant species which synthesize large amounts of oils in plant seeds, are an important source of oils both for edible and industrial uses.

A wide range of novel vegetable oils compositions and/or improved means to obtain or manipulate fatty acid compositions, from biosynthetic or natural plant sources, are needed for a variety of intended uses. Plant breeding, even with mutagenesis, cannot meet this need and provide for the introduction of any oil traits which are outside of the target plant's gene pool.

Various oils compositions are now in demand. For example, edible oil sources containing the minimum possible amounts of saturates, palmitate (C16:0) and stearate (C18:0) saturated fatty acids, are desired for dietary reasons and alternatives to current sources of highly saturated oil products, such as tropical oils, are also needed. Generating a spread of C4, C6 and C8 short chain 3-keto fatty acids could become a key improvement in polyhydroxybutyrate (PHB)-based biodegradable plastics made in bacteria and plants. Medium-chain fatty acids have special importance in the detergent and lubricant industries or in the formulation of edible oils with reduced caloric value or other health benefits. See for example, U.S. Pat. No. 4,863,753 and Barch, A. C. & Babayan, V. K., *Am. J. Clin. Nat.* (1982) 36:950-962. Longer chain fatty acids may have certain other utilities, i.e., C16 and C18 have particular uses in margarine and other solid oil-based products and very long chain fatty acids also have specialized uses, i.e., C22 is used to make peanut butter smoother. As such, a ready source of a variety of fatty acid lengths, including storage lipids which have incorporated differing chain length fatty acids in desired ratios, are desired for a variety of industrial and food use fields. Improved yield of current oilseed crops and the development of novel plant fatty acid compositions and oils products are also needed. Examples of novel plant fatty acid and oils products include fatty alcohols, epoxy fatty acids (e.g., biodegradable paint thinner), long chain liquid wax (e.g., jojoba oil substitute), hydroxylated fatty acids (motor lubricants) or cyclopropanated fatty acids (motor lubricants).

There is a need for improved means to obtain or manipulate compositions fatty acids from biosynthetic or natural plant sources. For example, novel oil products, improved sources of synthetic triacylglycerols (triglycerides), alternative sources of commercial oils, such as tropical oils (i.e., palm kernel and coconut oils), and plant oils found in trace amounts from natural sources are desired for a variety of industrial and food uses. Or, the ability to increase total oil production in plants may provide for novel applications of seed oils for use in human and animal nutrition.

SUMMARY OF THE INVENTION

The present invention is directed to fatty acid β-oxidation polynucleotides, and in particular to acyl-CoA oxidase (ACOX) polynucleotides. The present invention further provides 3-ketoacyl-CoA thiolase (thiolase) polynucleotides. The polynucleotides of the present invention include those derived from plant sources.

One aspect of the present invention relates to oligonucleotides which include partial or complete ACOX or thiolase encoding sequences.

It is also an aspect of the present invention to provide recombinant DNA constructs which can be used for transcription or transcription and translation (expression) of ACOX and/or thiolase. In particular, constructs are provided which are capable of transcription or transcription and translation in host cells. Particularly preferred constructs are those capable of suppression of endogenous host cell ACOX and/or thiolase.

In another aspect of the present invention, methods are provided for production of ACOX and or thiolase in a host cell or progeny thereof. In particular, host cells are transformed or transfected with a DNA construct which can be used for transcription or transcription and translation of ACOX and/or thiolase. The recombinant cells which contain ACOX and/or thiolase are also part of the present invention.

In a further aspect, the present invention relates to methods of using polynucleotide and polypeptide sequences to modify the fatty acid content as well as composition, particularly in seed tissue of oilseed crops. Plant cells having such a modified fatty acid content are also contemplated herein.

In yet a further aspect, the present invention relates to methods of using polynucleotide and polypeptide sequences to inhibit or delay the germination of seeds.

The modified plants, seeds and oils obtained by the expression of the plant ACOX proteins are also considered part of the invention.

DETAILED DESCRIPTION OF THE INVENTION

Figure 1:
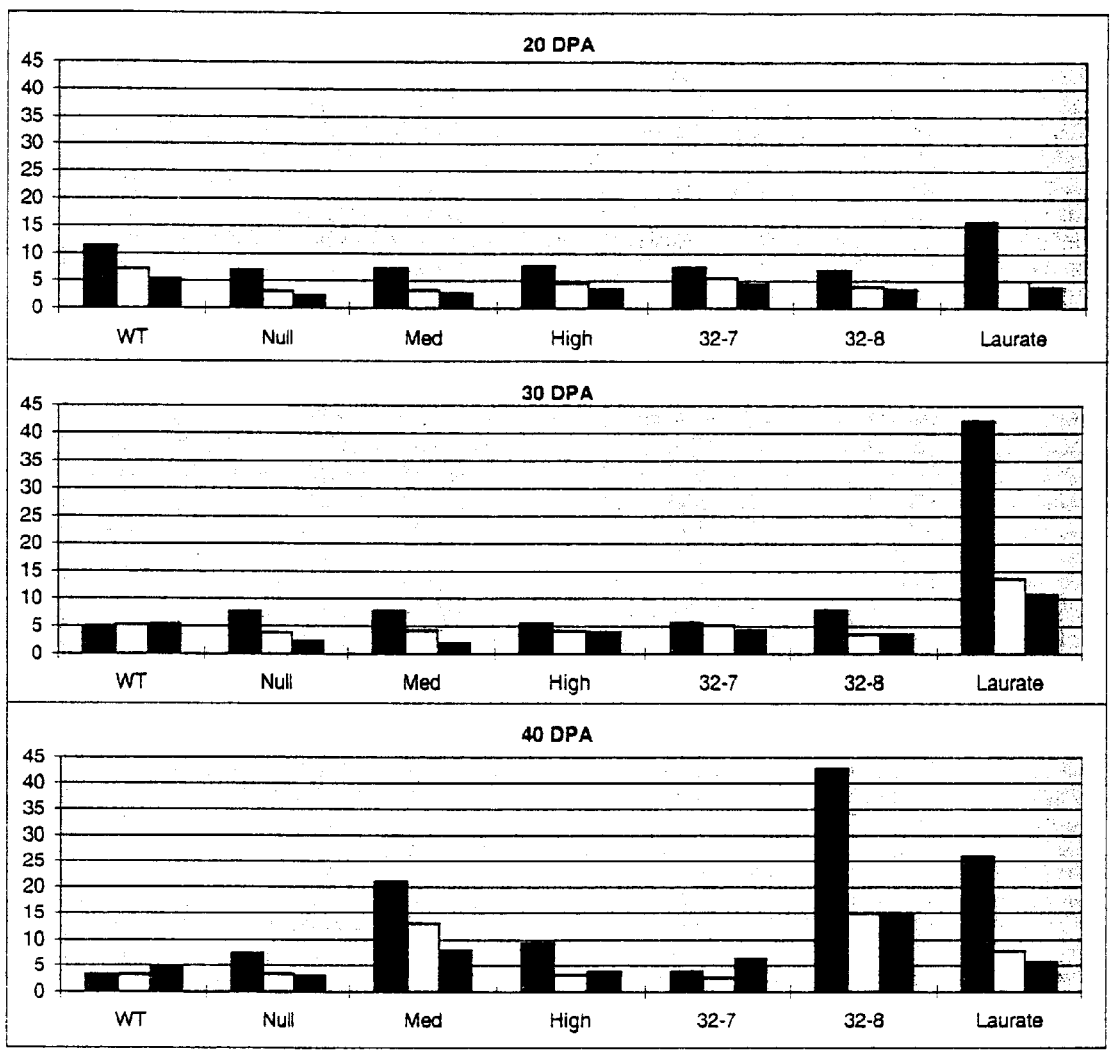
FIG. 1 Provides ACOX activity comparisons in 20, 30 and 40 day post anthesis (dpa) developing seeds of wild-type Brassica, null lines, medium and high level MCFA containing lines, and laurate producing lines. Each line was examined for short chain specific ACOX activity (6:0 CoA), medium chain specific ACOX activity (12:0 CoA), and long chain specific activity (16:0 CoA), represented by the left bar, middle bar and right bar on the graph respectively.
Figure 1:
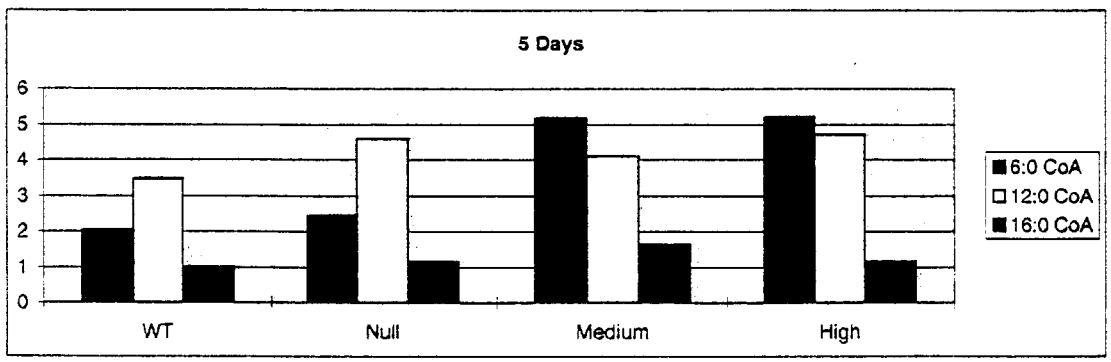

In accordance with the subject invention, polynucleotides and polypeptides involved in plant fatty acid β-oxidation and methods for the use of such polynucleotides and polypeptides are provided. In particular, polynucleotides and polypeptides related to acyl-CoA oxidase polynucleotides. The present invention further provides 3-ketoacyl-CoA thiolase polynucleotides and polypeptides.

Beta-oxidation is responsible for the catabolism of fatty acids to produce succinate for the production of sucrose. Fatty acyl-CoA is the substrate for fatty acid β-oxidation in peroxisomes and mitochondria, which consists of four steps. The first step of β-oxidation is catalyzed by Acyl-CoA oxidase (hereinafter also referred to as ACOX). The second and third steps are catalyzed by a single enzyme which has both enoyl-CoA hydratase and β-hydroxyacyl-CoA dehydrogenase activities. The fourth step is catalyzed by 3-ketoacyl-CoA thiolase (herein after also referred to as thiolase). The acetyl-CoA produced as a result of β-oxidation is metabolized further to produce succinate by the glyoxylate pathway.

A first aspect of the present invention relates to isolated polynucleotides involved in plant fatty acid β-oxidation. In particular, isolated ACOX and thiolase polynucleotides are provided. The polynucleotide sequences of the present invention include isolated polynucleotides that encode the polypeptides of the invention having a deduced amino acid sequence selected from the group of sequences set forth in the Sequence Listing and to other polynucleotide sequences closely related to such sequences and variants thereof.

The invention provides a polynucleotide sequence identical over its entire length to each coding sequence as set forth in the Sequence Listing. The invention also provides the coding sequence for the mature polypeptide or a fragment thereof, as well as the coding sequence for the mature polypeptide or a fragment thereof in a reading frame with other coding sequences, such as those encoding a leader or secretory sequence, a pre-, pro-, or prepro-protein sequence. The polynucleotide can also include non-coding sequences, including for example, but not limited to, non-coding 5' and 3' sequences, such as the transcribed, untranslated sequences, termination signals, ribosome binding sites, sequences that stabilize mRNA, introns, polyadenylation signals, and additional coding sequence that encodes additional amino acids. For example, a marker sequence can be included to facilitate the purification of the fused polypeptide. Polynucleotides of the present invention also include polynucleotides comprising a structural gene and the naturally associated sequences that control gene expression.

The invention also includes polynucleotides of the formula:

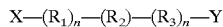

wherein, at the 5' end, X is hydrogen, and at the 3' end, Y is hydrogen or a metal, $R_1$ and $R_3$ are any nucleic acid residue, n is an integer between 1 and 3000, preferably between 1 and 1000 and $R_2$ is a nucleic acid sequence of the invention, particularly a nucleic acid sequence selected from the group set forth in the Sequence Listing and preferably SEQ ID NOs: 1, 3, 5, 7, 9, 11, 13, 15, 17, 19, 21, and 23. In the formula, $R_2$ is oriented so that its 5' end residue is at the left, bound to $R_1$, and its 3' end residue is at the right, bound to $R_3$. Any stretch of nucleic acid residues denoted by either R group, where R is greater than 1, may be either aheteropolymer or a homopolymer, preferably a heteropolymer.

The invention also relates to variants of the polynucleotides described herein that encode for variants of the polypeptides of the invention. Variants that are fragments of the polynucleotides of the invention can be used to synthesize full-length polynucleotides of the invention. Preferred embodiments are polynucleotides encoding polypeptide variants wherein 5 to 10, 1 to 5, 1 to 3, 2, 1 or no amino acid residues of a polypeptide sequence of the invention are substituted, added or deleted, in any combination. Particularly preferred are substitutions, additions, and deletions that are silent such that they do not alter the properties or activities of the polynucleotide or polypeptide.

Further preferred embodiments of the invention that are at least 50%, 60%, or 70% identical over their entire length to a polynucleotide encoding a polypeptide of the invention, and polynucleotides that are complementary to such polynucleotides. More preferable are polynucleotides that comprise a region that is at least 80% identical over its entire length to a polynucleotide encoding a polypeptide of the invention and polynucleotides that are complementary thereto. In this regard, polynucleotides at least 90% identical over their entire length are particularly preferred, those at least 95% identical are especially preferred. Further, those with at least 97% identity are highly preferred and those with at least 98% and 99% identity are particularly highly preferred, with those at least 99% being the most highly preferred.

Preferred embodiments are polynucleotides that encode polypeptides that retain substantially the same biological function or activity as the mature polypeptides encoded by the polynucleotides set forth in the Sequence Listing.

The invention further relates to polynucleotides that hybridize to the above-described sequences. In particular, the invention relates to polynucleotides that hybridize under stringent conditions to the above-described polynucleotides. As used herein, the terms "stringent conditions" and "stringent hybridization conditions" mean that hybridization will generally occur if there is at least 95% and preferably at least 97% identity between the sequences. An example of stringent hybridization conditions is overnight incubation at 42° C. in a solution comprising 50% formamide, 5×SSC (150 mM NaCl, 15 mM trisodium citrate), 50 mM sodium phosphate (pH 7.6), 5×Denhardt's solution, 10% dextran sulfate, and 20 micrograms/milliliter denatured, sheared salmon sperm DNA, followed by washing the hybridization support in 0.1×SSC at approximately 65° C. Other hybridization and wash conditions are well known and are exemplified in Sambrook, et al., Molecular Cloning: A Laboratory Manual, Second Edition, cold Spring Harbor, N.Y. (1989), particularly Chapter 11.

One skilled in the art will readily recognize that antibody preparations, nucleic acid probes (DNA and RNA) and the like may be prepared and used to screen and recover "homologous" or "related" sequences from a variety of plant sources. Homologous sequences are found when there is an identity of sequence, which may be determined upon comparison of sequence information, nucleic acid or amino acid, or through hybridization reactions between a known ACOX or thiolase and a candidate source. Conservative changes, such as Glu/Asp, Val/Ile, Ser/Thr, Arg/Lys and Gln/Asn may also be considered in determining sequence homology. Amino acid sequences are considered homologous by as little as 25% sequence identity between the two complete mature proteins. (See generally, Doolittle, R. F., *OF URFS and ORFS* (University Science Books, CA, 1986.).

Thus, other ACOXs and thiolases may be obtained from the specific sequences provided herein. Furthermore, it will be apparent that one can obtain natural and synthetic sequences, including modified amino acid sequences and starting materials for synthetic-protein modeling from the exemplified ACOX and thiolase sequences and from sequences which are obtained through the use of such exemplified sequences. Modified amino acid sequences include sequences which have been mutated, truncated, increased and the like, whether such sequences were partially or wholly synthesized. Sequences which are actually purified from plant preparations or are identical or encode identical proteins thereto, regardless of the method used to obtain the protein or sequence, are equally considered naturally derived.

For immunological screening, antibodies to the protein can be prepared by injecting rabbits or mice with the purified protein or portion thereof, such methods of preparing antibodies being well known to those in the art. Either monoclonal or polyclonal antibodies can be produced, although typically polyclonal antibodies are more useful for gene isolation. Western analysis may be conducted to determine that a related protein is present in a crude extract of the desired plant species, as determined by cross-reaction with the antibodies to the encoded proteins. When cross-reactivity is observed, genes encoding the related proteins are isolated by screening expression libraries representing the desired plant species. Expression libraries can be constructed in a variety of commercially available vectors, including lambda gt11, as described in Sambrook, et al. (*Molecular Cloning: A Laboratory Manual,* Second Edition (1989) Cold Spring Harbor Laboratory, Cold Spring Harbor, N.Y.).

The invention also provides a polynucleotide consisting essentially of a polynucleotide sequence obtainable by screening an appropriate library containing the complete gene for a polynucleotide sequence set for in the Sequence Listing under stringent hybridization conditions with a probe having the sequence of said polynucleotide sequence or a fragment thereof; and isolating said polynucleotide sequence. Fragments useful for obtaining such a polynucleotide include, for example, probes and primers as described herein.

As discussed herein regarding polynucleotide assays of the invention, for example, polynucleotides of the invention can be used as a hybridization probe for RNA, cDNA, or genomic DNA to isolate full length cDNAs or genomic clones encoding a polypeptide and to isolate cDNA or genomic clones of other genes that have a high sequence similarity to a polynucleotide set forth in the Sequence Listing. Such probes will generally comprise at least 15 bases. Preferably such probes will have at least 30 bases and can have at least 50 bases. Particularly preferred probes will have between 30 bases and 50 bases, inclusive.

The coding region of each gene that comprises or is comprised by a polynucleotide sequence set forth in the Sequence Listing may be isolated by screening using a DNA sequence provided in the Sequence Listing to synthesize an oligonucleotide probe. A labeled oligonucleotide having a sequence complementary to that of a gene of the invention is then used to screen a library of cDNA, genomic DNA or mRNA to identify members of the library which hybridize to the probe. For example, synthetic oligonucleotides are prepared which correspond to the ACOX EST sequences. The oligonucleotides are used as primers in polymerase chain reaction (PCR) techniques to obtain 5' and 3' terminal sequence of ACOX genes. Alternatively, where oligonucleotides of low degeneracy can be prepared from particular ACOX peptides, such probes may be used directly to screen gene libraries for ACOX gene sequences. In particular, screening of cDNA libraries in phage vectors is useful in such methods due to lower levels of background hybridization.

Typically, a sequence obtainable from the use of nucleic acid probes will show 60–70% sequence identity between the target sequence and the encoding sequence used as a probe. However, lengthy sequences with as little as 50–60% sequence identity may also be obtained. The nucleic acid probes may be a lengthy fragment of the nucleic acid sequence, or may also be a shorter, oligonucleotide probe. When longer nucleic acid fragments are employed as probes (greater than about 100 bp), one may screen at lower stringencies in order to obtain sequences from the target sample which have 20–50% deviation (i.e., 50–80% sequence homology) from the sequences used as probe. Oligonucleotide probes can be considerably shorter than the entire nucleic acid sequence encoding an ACOX or thiolase enzyme, but should be at least about 10, preferably at least about 15, and more preferably at least about 20 nucleotides. A higher degree of sequence identity is desired when shorter regions are used as opposed to longer regions. It may thus be desirable to identify regions of highly conserved amino acid sequence to design oligonucleotide probes for detecting and recovering other related ACOX and thiolase genes. Shorter probes are often particularly useful for polymerase chain reactions (PCR), especially when highly conserved sequences can be identified. (See, Gould, et al., *PNAS USA* (1989) 86:1934–1938.).

Another aspect of the present invention relates to plant fatty acid β-oxidation polypeptides. In particular, ACOX and thiolase polypepetides are provided. Such polypeptides include isolated polypeptides set forth in the Sequence Listing, as well as polypeptides and fragments thereof, particularly those polypeptides which exhibit ACOX or thiolase activity and also those polypeptides which have at least 50%, 60% or 70% identity, preferably at least 80% identity, more preferably at least 90% identity, and most preferably at least 95% identity to a polypeptide sequence selected from the group of sequences set forth in the Sequence Listing, and also include portions of such polypeptides, wherein such portion of the polypeptide preferably includes at least 30 amino acids and more preferably includes at least 50 amino acids.

"Identity", as is well understood in the art, is a relationship between two or more polypeptide sequences or two or more polynucleotide sequences, as determined by comparing the sequences. In the art, "identity" also means the degree of sequence relatedness between polypeptide or polynucleotide sequences, as determined by the match between strings of such sequences. "Identity" can be readily calculated by known methods including, but not limited to, those described in *Computational Molecular Biology,* Lesk, A. M., ed., Oxford University Press, New York (1988); *Biocomputing: Informatics and Genome Projects,* Smith, D. W., ed., Academic Press, New York, 1993; *Computer Analysis of Sequence Data, Part I,* Griffin, A. M. and Griffin, H. G., eds., Humana Press, New Jersey (1994); *Sequence Analysis in Molecular Biology,* von Heinje, G., Academic Press (1987); *Sequence Analysis Primer,* Gribskov, M. and Devereux, J., eds., Stockton Press, New York (1991); and Carillo, H., and Lipman, D., SIAM *J Applied Math*, 48:1073 (1988). Methods to determine identity are designed to give the largest match between the sequences tested. Moreover, methods to determine identity are codified in publicly available programs. Computer programs which can be used to determine identity between two sequences include, but are not limited to, GCG (Devereux, J., et al., *Nucleic Acids Research* 12(1):387 (1984); suite of five BLAST programs, three designed for nucleotide sequences queries (BLASTN, BLASTX, and TBLASTX) and two designed for protein sequence queries (BLASTP and TBLASTN) (Coulson, *Trends in Biotechnology*, 12: 76–80 (1994); Birren, et al., *Genome Analysis*, 1: 543–559 (1997)). The BLAST X program is publicly available from NCBI and other sources (*BLAST Manual*, Altschul, S., et al., NCBI NLM NIH, Bethesda, Md. 20894; Altschul, S., et al., *J. Mol. Biol.*, 215:403–410 (1990)). The well known Smith Waterman algorithm can also be used to determine identity.

Parameters for polypeptide sequence comparison typically include the following:

Algorithm: Needleman and Wunsch, *J. Mol. Biol.* 48:443–453 (1970)

Comparison matrix: BLOSSUM62 from Hentikoff and Hentikoff, *Proc. Natl. Acad. Sci USA* 89:10915–10919 (1992)

Gap Penalty: 12

Gap Length Penalty: 4

A program which can be used with these parameters is publicly available as the "gap" program from Genetics Computer Group, Madison Wis. The above parameters along with no penalty for end gap are the default parameters for peptide comparisons.

Parameters for polynucleotide sequence comparison include the following:

Algorithm: Needleman and Wunsch, J. Mol. Biol. 48:443–453 (1970)

Comparison matrix: matches=+10; mismatches=0

Gap Penalty: 50

Gap Length Penalty: 3

A program which can be used with these parameters is publicly available as the "gap" program from Genetics Computer Group, Madison Wis. The above parameters are the default parameters for nucleic acid comparisons.

The invention also includes polypeptides of the formula:

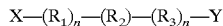

$$X—(R_1)_n—(R_2)—(R_3)_n—Y$$

wherein, at the amino terminus, X is hydrogen, and at the carboxyl terminus, Y is hydrogen or a metal, $R_1$ and $R_3$ are any amino acid residue, n is an integer between 1 and 1000, and $R_2$ is an amino acid sequence of the invention, particularly an amino acid sequence selected from the group set forth in the Sequence Listing and preferably SEQ ID NOs: 2, 4, 6, 8, 10, 12, 14, 16, 18, 20, 22, and 24. In the formula, $R_2$ is oriented so that its amino terminal residue is at the left, bound to $R_1$, and its carboxy terminal residue is at the right, bound to $R_3$. Any stretch of amino acid residues denoted by either R group, where R is greater than 1, may be either aheteropolymer or a homopolymer, preferably a heteropolymer.

Polypeptides of the present invention include isolated polypeptides encoded by a polynucleotide comprising a sequence selected from the group set forth in the Sequence Listing and preferably SEQ ID NOs: 2, 4, 6, 8, 10, 12, 14, 16, 18, 20, 22, and 24.

The polypeptides of the present invention can be mature protein or can be part of a fusion protein.

Fragments and variants of the polypeptides are also considered to be a part of the invention. A fragment is a variant polypeptide which has an amino acid sequence that is entirely the same as part but not all of the amino acid sequence of the previously described polypeptides. The fragments can be "free-standing" or comprised within a larger polypeptide of which the fragment forms a part or a region, most preferably as a single continuous region. Preferred fragments are biologically active fragments which are those fragments that mediate activities of the polypeptides of the invention, including those with similar activity or improved activity or with a decreased activity. Also included are those fragments that antigenic or immunogenic in an animal, particularly a human.

Variants of the polypeptide also include polypeptides that vary from the sequences set forth in the Sequence Listing by conservative amino acid substitutions, substitution of a residue by another with like characteristics. In general, such substitutions are among Ala, Val, Leu and Ile; between Ser and Thr; between Asp and Glu; between Asn and Gln; between Lys and Arg; or between Phe and Tyr. Particularly preferred are variants in which 5 to 10; 1 to 5; 1 to 3 or one amino acid(s) are substituted, deleted, or added, in any combination.

Variants that are fragments of the polypeptides of the invention can be used to produce the corresponding full length polypeptide by peptide synthesis. Therefore, these variants can be used as intermediates for producing the full-length polypeptides of the invention.

The polynucleotides and polypeptides of the invention can be used, for example, in the transformation of host cells, such as plant host cells, as further discussed herein.

The invention also provides polynucleotides that encode a polypeptide that is a mature protein plus additional amino or carboxyl-terminal amino acids, or amino acids within the mature polypeptide (for example, when the mature form of the protein has more than one polypeptide chain). Such sequences can, for example, play a role in the processing of a protein from a precursor to a mature form, allow protein transport, shorten or lengthen protein half-life, or facilitate manipulation of the protein in assays or production. It is contemplated that cellular enzymes can be used to remove any additional amino acids from the mature protein.

A precursor protein, having the mature form of the polypeptide fused to one or more prosequences may be an inactive form of the polypeptide. The inactive precursors generally are activated when the prosequences are removed. Some or all of the prosequences may be removed prior to activation. Such precursor protein are generally called proproteins.

Once the desired nucleic acid sequence is obtained, it may be manipulated in a variety of ways. Where the sequence involves non-coding flanking regions, the flanking regions may be subjected to resection, mutagenesis, etc. Thus, transitions, transversions, deletions, and insertions may be performed on the naturally occurring sequence. In addition, all or part of the sequence may be synthesized. In the structural gene, one or more codons may be modified to provide for a modified amino acid sequence, or one or more codon mutations may be introduced to provide for a convenient restriction site or other purpose involved with construction or expression. The structural gene may be further modified by employing synthetic adapters, linkers to introduce one or more convenient restriction sites, or the like.

Of interest in the present invention is the use of the polynucleotide sequences in the preparation of DNA constructs. Furthermore, of particular interest is the use of the nucleic acid sequences of the present invention for the production of expression cassettes for use in transformation of host cells. Such transformed host cells can provide a ready source of the enzyme for a wide variety of uses, including, but not limited to, enzyme assays, fermentation, biotransformation, and the like.

Suitable host cells include both prokaryotic and eukaryotic cells. In particular, host cells for use in the methods of the present invention include fungal cells, including yeast, mammalian cells, insect cells, bacterial cells, and plant cells.

Of particular interest is the use of the nucleotide sequences in recombinant DNA constructs to direct the transcription or transcription and translation (expression) of the ACOX sequences of the present invention in a host plant cell. The expression constructs generally comprise a promoter functional in a host plant cell operably linked to a nucleic acid sequence encoding an ACOX of the present invention and a transcriptional termination region functional in a host plant cell.

Those skilled in the art will recognize that there are a number of promoters which are functional in plant cells, and have been described in the literature. Chloroplast and plastid specific promoters, chloroplast or plastid functional promoters, and chloroplast or plastid operable promoters are also envisioned.

One set of promoters are constitutive promoters such as the CaMV35S or FMV35S promoters that yield high levels of expression in most plant organs. Enhanced or duplicated versions of the CaMV35S and FMV35S promoters are useful in the practice of this invention (Odell, et al. (1985) *Nature* 313:810–812; Rogers, U.S. Pat. No. 5,378,619). In addition, it may also be preferred to bring about expression of the ACOX gene in specific tissues of the plant, such as leaf, stem, root, tuber, seed, fruit, etc., and the promoter chosen should have the desired tissue and developmental specificity.

Of particular interest is the expression of the nucleic acid sequences of the present invention from transcription initiation regions which are preferentially expressed in a plant seed tissue. Examples of such seed preferential transcription initiation sequences include those sequences derived from sequences encoding plant storage protein genes or from genes involved in fatty acid biosynthesis in oilseeds. Examples of such promoters include the 5' regulatory regions from such genes as napin (Kridl et al., *Seed Sci. Res.* 1:209:219 (1991)), phaseolin, zein, soybean trypsin inhibitor, ACP, stearoyl-ACP desaturase, soybean α' subunit of β-conglycinin (soy 7s, (Chen et al., *Proc. Natl. Acad. Sci.,* 83:8560–8564 (1986))) and oleosin.

It may be advantageous to direct the localization of proteins conferring ACOX to a particular subcellular compartment, for example, to the mitochondrion, peroxisomes, endoplasmic reticulum, vacuoles, chloroplast or other plastidic compartment. For example, where the genes of interest of the present invention will be targeted to the peroxisome the constructs will also employ the use of peroxisome targeting sequences. Such sequences are referred to herein as peroxisome targeting sequences (PTS). Such peroxisome targeting sequences are known in the art, see for example Olsen, et al. (1993) *Plant Cell* 5:941–952. Alternatively, the targeting sequence can be obtained from the native ACOX or thiolase protein. Sequences for targeting preferred proteins to other specific subcellular compartments are described, for example, by; Von Heijne et al. (1991) *Plant Mol. Biol. Rep.* 9:104–126; Clark et al. (1989) *J. Biol. Chem.* 264:17544–17550; della-Cioppa et al. (1987) *Plant Physiol.* 84:965–968; Romer et al. (1993) *Biochem. Biophys. Res Commun.* 196:1414–1421; and, Shah et al. (1986) *Science* 233:478–481.

Depending upon the intended use, the expression constructs may contain the nucleic acid sequence which encodes the entire ACOX or thiolase protein, or a portion thereof. For example, where antisense inhibition of a given ACOX or thiolase protein is desired, the entire ACOX sequence is not required. Furthermore, where ACOX or thiolase sequences used in constructs are intended for use as probes, it may be advantageous to prepare constructs containing only a particular portion of a ACOX or thiolase encoding sequence, for example a sequence which is discovered to encode a highly conserved ACOX or thiolase region.

The skilled artisan will recognize that there are various methods for the inhibition of expression of endogenous sequences in a host cell. Such methods include, but are not limited to antisense suppression (Smith, et al. (1988) *Nature* 334:724–726) , co-suppression (Napoli, et al. (1989) *Plant Cell* 2:279–289), ribozymes (PCT Publication WO 97/10328), and combinations of sense and antisense Waterhouse, et al. (1998) *Proc. NatL Acad. Sci. USA* 95:13959–13964. Methods for the suppression of endogenous sequences in a host cell typically employ the use of at least a portion of the sequence to be suppressed in the expression construct. Such sequences may be homologous to coding as well as non-coding regions of the endogenous sequence. Depending on the method of suppression employed, sequences complementary to the host cells endogenous sequence can be used in the expression constructs.

Regulatory transcript termination regions may be provided in plant expression constructs of this invention as well. Transcript termination regions may be provided by the DNA sequence encoding the ACOX or thiolase of the present invention or a convenient transcription termination region derived from a different gene source, for example, the transcript termination region which is naturally associated with the transcript initiation region. The skilled artisan will recognize that any convenient transcript termination region which is capable of terminating transcription in a plant cell may be employed in the constructs of the present invention.

Alternatively, constructs may be prepared to direct the expression of the ACOX or thiolase sequences directly from the host plant cell plastid. Such constructs and methods are known in the art and are generally described, for example, in Svab, et al. (1990) *Proc. Natl. Acad. Sci. USA* 87:8526–8530 and Svab and Maliga (1993) *Proc. Natl. Acad. Sci. USA* 90:913–917 and in U.S. Pat. No. 5,693,507.

A plant cell, tissue, organ, or plant into which the recombinant DNA constructs containing the expression constructs have been introduced is considered transformed, transfected, or transgenic. A transgenic or transformed cell or plant also includes progeny of the cell or plant and progeny produced from a breeding program employing such a transgenic plant as a parent in a cross and exhibiting an altered phenotype resulting from the presence of a ACOX nucleic acid sequence.

Plant expression or transcription constructs having a sequence of the present invention as the DNA sequence of interest for increased or decreased expression thereof may be employed with a wide variety of plant life, particularly, plant life involved in the production of vegetable oils for edible and industrial uses. Most especially preferred are temperate oilseed crops. Plants of interest include, but are not limited to, rapeseed (Canola and High Erucic Acid varieties), sunflower, safflower, cotton, soybean, peanut, coconut and oil palms, and corn. Depending on the method for introducing the recombinant constructs into the host cell, other DNA sequences may be required. Importantly, this invention is applicable to dicotyledyons and monocotyledons species alike and will be readily applicable to new and/or improved transformation and regulation techniques.

Of particular interest, is the use of the expression constructs of the present invention in plants to produce plants or plant parts, including, but not limited to leaves, stems, roots, reproductive, and seed, with a modified fatty acid composition and/or yield of the fatty acid content.

Thus, the present invention provides methods for enhancing the content or altering the composition of fatty acids and compounds containing such fatty acids, such as oils, waxes, fats, and storage proteins. Such methods employ the use of the expression constructs described herein for the modification of the host plant cell's β-oxidation pathway.

The present invention further provides methods for inhibiting or postponing germination in seeds having an introduced expression construct providing for the suppression of the host cells endogenous ACOX and/or thiolase in the seed of the host cell.

The present invention also provides methods for the production of particular fatty acids in host plant cells.

The expression constructs of the present invention can be used in conjunction with additional expression constructs employing nucleic acid sequences encoding fatty acid biosynthetic proteins. Such sequences encoding fatty acid biosynthetic proteins are known in the art and include, but are not limited to, thioesterases (see for example, U.S. Pat. No. 5,667,997), β-ketoacyl-ACP synthases (KAS)(see for example U.S. Pat. No. 5,475,099), desaturases, and the like.

Furthermore, more than one additional sequence encoding fatty acid biosynthetic protein can be used in conjunction with the expression constructs of the present invention. For example, the expression constructs of the present invention can be used in conjunction with expression constructs providing the expression of a thioesterase and an expression construct providing for the expression of a β-ketoacyl-ACP synthase (see for example, PCT Publication WO 98/46776).

Thus, the present invention also provides methods for the production of particular fatty acids in a host plant cell. Such methods use the expression constructs of the present invention in conjunction with at least one additional expression construct having a nucleic acid sequence encoding a protein involved in fatty acid biosynthesis. Preferably the ACOX and/or thiolase expression construct used provides for the suppression of endogenous host plant cells ACOX and/or thiolase. The additional expression constructs employed can provide for the expression or suppression of fatty acid biosynthesis proteins.

It is contemplated that the gene sequences may be synthesized, either completely or in part, especially where it is desirable to provide plant-preferred sequences. Thus, all or a portion of the desired structural gene (that portion of the gene which encodes the protein) may be synthesized using codons preferred by a selected host. Host-preferred codons may be determined, for example, from the codons used most frequently in the proteins expressed in a desired host species.

To confirm the activity and specificity of the proteins encoded by the identified nucleic acid sequences as ACOX or thiolase proteins, in vitro assays are performed in insect cell cultures using baculovirus expression systems. Such baculovirus expression systems are known in the art and are described by Lee, et al. U.S. Pat. No. 5,348,886, the entirety of which is herein incorporated by reference.

In addition, other expression constructs may be prepared to assay for protein activity utilizing different expression systems. Such expression constructs are transformed into yeast or prokaryotic host and assayed for ACOX or thiolase activity. Such expression systems are known in the art and are readily available through commercial sources.

The method of transformation in obtaining such transgenic plants is not critical to the instant invention, and various methods of plant transformation are currently available. Furthermore, as newer methods become available to transform crops, they may also be directly applied hereunder. For example, many plant species naturally susceptible to Agrobacterium infection may be successfully transformed via tripartite or binary vector methods of Agrobacterium mediated transformation. In many instances, it will be desirable to have the construct bordered on one or both sides by T-DNA, particularly having the left and right borders, more particularly the right border. This is particularly useful when the construct uses *A. tumefaciens* or *A. rhizogenes* as a mode for transformation, although the T-DNA borders may find use with other modes of transformation. In addition, techniques of microinjection, DNA particle bombardment, and electroporation have been developed which allow for the transformation of various monocot and dicot plant species.

Normally, included with the DNA construct will be a structural gene having the necessary regulatory regions for expression in a host and providing for selection of transformant cells. The gene may provide for resistance to a cytotoxic agent, e.g. antibiotic, heavy metal, toxin, etc., complementation providing prototrophy to an auxotrophic host, viral immunity or the like. Depending upon the number of different host species the expression construct or components thereof are introduced, one or more markers may be employed, where different conditions for selection are used for the different hosts.

Where Agrobacterium is used for plant cell transformation, a vector may be used which may be introduced into the Agrobacterium host for homologous recombination with T-DNA or the Ti- or Ri-plasmid present in the Agrobacterium host. The Ti- or Ri-plasmid containing the T-DNA for recombination may be armed (capable of causing gall formation) or disarmed (incapable of causing gall formation), the latter being permissible, so long as the vir genes are present in the transformed Agrobacterium host. The armed plasmid can give a mixture of normal plant cells and gall.

In some instances where Agrobacterium is used as the vehicle for transforming host plant cells, the expression or transcription construct bordered by the T-DNA border region (s) will be inserted into a broad host range vector capable of replication in *E. coli* and Agrobacterium, there being broad host range vectors described in the literature. Commonly used is pRK2 or derivatives thereof. See, for example, Ditta, et al., (*Proc. Nat. Acad. Sci., U.S.A.* (1980) 77:7347–7351) and EPA 0 120 515, which are incorporated herein by reference. Alternatively, one may insert the sequences to be expressed in plant cells into a vector containing separate replication sequences, one of which stabilizes the vector in *E. coli,* and the other in Agrobacterium. See, for example, McBride and Summerfelt (*Plant Mol. Biol.* (1990) 14:269–276), wherein the pRiHRI (Jouanin, et al., *Mol. Gen. Genet.* (1985) 201:370–374) origin of replication is utilized and provides for added stability of the plant expression vectors in host Agrobacterium cells.

Included with the expression construct and the T-DNA will be one or more markers, which allow for selection of transformed Agrobacterium and transformed plant cells. A number of markers have been developed for use with plant cells, such as resistance to chloramphenicol, kanamycin, the aminoglycoside G418, hygromycin, or the like. The particular marker employed is not essential to this invention, one or another marker being preferred depending on the particular host and the manner of construction.

For transformation of plant cells using Agrobacterium, explants may be combined and incubated with the transformed Agrobacterium for sufficient time for transformation, the bacteria killed, and the plant cells cultured in an appropriate selective medium. Once callus forms, shoot formation can be encouraged by employing the appropriate plant hormones in accordance with known methods and the shoots transferred to rooting medium for regeneration of plants. The plants may then be grown to seed and the seed used to establish repetitive generations and for isolation of vegetable oils.

There are several possible ways to obtain the plant cells of this invention which contain multiple expression constructs. Any means for producing a plant comprising a construct having a DNA sequence encoding the expression construct of the present invention, and at least one other construct having another DNA sequence encoding an enzyme are encompassed by the present invention. For example, the expression construct can be used to transform a plant at the same time as the second construct either by inclusion of both expression constructs in a single transformation vector or by using separate vectors, each of which express desired genes. The second construct can be introduced into a plant which has already been transformed with the ACOX or thiolase expression construct, or alternatively, transformed plants, one expressing the ACOX or thiolase construct and one expressing the second construct, can be crossed to bring the constructs together in the same plant.

Thus, by expression of the nucleic acid sequences encoding the plant β-oxidation sequences of the present invention in a host cell, it is possible to modify the lipid content and/or composition of the host cell. Furthermore, it is also possible to inhibit or delay the germination of seeds of plant containing the expression constructs of the present invention.

The invention now being generally described, it will be more readily understood by reference to the following examples which are included for purposes of illustration only and are not intended to limit the present invention.

EXAMPLES

Example 1

Characterization of Developing and Germinating Seeds

Seeds of Brassica plants containing the constructs pCGN5401 for the expression of ChKAS A and pCGN4804 for the expression of the *Cuphea pulcheriama* FatB1 thioesterase (described in WO 98/46776, the entirety of which is incorporated herein by reference) were analyzed for activity of enzymes involved in β-oxidation. Acyl-CoA oxidase assays were performed on wild-type *Brassica napus* plants as well as on transgenic plants containing different levels of medium chain fatty acids. Plants were grouped into three groups, high level MCFA containing lines, medium level MCFA containing lines, and null lines.

The results demonstrate that short, medium, and long chain acyl-CoA oxidase enzymes are active at all time points in all seeds examined during seed development. The short chain ACOX is the most active enzyme at all time points, with the exception of 40 days post anthesis (dpa) wild-type seeds. The highest activity for short chain ACOX as contrasted to the wild-type is measured at 30 dpa laurate producing seed (U.S. Pat. No. 5,344,771, the entirety of which is incorporated herein by reference) and 40 dpa MCFA (lines containing pCGN5401 and pCGN4804) (FIG. 1).

Furthermore, five day old germinating seeds from wild-type, null, medium, and high MCFA producing Brassica lines were assayed for ACOX activity. The results demonstrate that in MCFA producing seeds, short chain ACOX was most active whereas in the wild-type and the null, the medium chain ACOX showed the highest activity (FIG. 1).

Example 2

Identification of Acyl CoA Oxidase and Thiolase Sequences

Nucleic acid sequences were identified in genomic DNA sequence databases using various ACOX sequences. The results of the searches in databases containing Arabidopsis sequences identified two un-annotated sequences related to ACOX and one un-annotated sequence related to peroxisomal thiolases. These sequences are referred to as At ACX1-1 (SEQ ID NO:3), At ACX3 (SEQ ID NO:7), and At PED1-1 (SEQ ID NO:13), respectively. In addition, related sequences are also identified in databases containing genomic DNA sequences from Brassica. These sequences are referred to as Br ACX1 (SEQ ID NO:17), Br ACX2 (SEQ ID NO:19), Br PED1 (SEQ ID NO:21), Br PKT2 (SEQ ID NO:23) and Br SACOX (SEQ ID NO:26).

Sequence alignments between the ACOX sequences identified herein and previously identified ACOX sequences are compared to identify the similarity between the sequences. Both nucleic acid as well as amino acid sequences are aligned.

Example 4

Expression Constructs

4A. *E. coli* Expression Constructs

Constructs are prepared to direct the expression of the Arabidopsis and Brassica ACOX and thiolase sequences in *E coli*. The entire coding region of the ACOX and thiolase sequence is amplified using polymerase chain reaction (PCR). The PCR products was subcloned into PQE30 (Qiagen). Double stranded DNA sequence was obtained to verify that no errors were introduced by PCR amplification. The plasmid pCGN10407 contains the coding sequence of AtACX2 for expression in *E. coli*. The plasmid pCGN10408 contains the coding sequence of BrACX2 for expression in *E. coli*. The plasmid pCGN10409 contains the coding sequence of AtACX3 for expression in *E. coli*. The plasmid pCGN10410 contains the coding sequence of AtACX1 for expression in *E. coli*. The plasmid pCGN10411 contains the coding sequence of AtACX1-1 for expression in *E. coli*. The plasmid pCGN10412 contains the coding sequence of BrACX1 for expression in *E. coli*.

4B. Plant Expression Construct Preparation

A plasmid containing the napin cassette derived from pCGN3223 (described in U.S. Pat. No. 5,639,790, the entirety of which is incorporated herein by reference) was modified to make it more useful for cloning large DNA fragments containing multiple restriction sites, and to allow the cloning of multiple napin fusion genes into plant binary transformation vectors. An adapter comprised of the self annealed oligonucleotide of sequence CGCGATTTAAATG-GCGCGCCCTGCAGGCGGCCGCCTG-CAGGGCGCGCCATTTAAAT (SEQ ID NO:25) was ligated into the cloning vector pBC SK+ (Stratagene) after digestion with the restriction endonuclease BssHII to construct vector pCGN7765. Plamids pCGN3223 and pCGN7765 were digested with NotI and ligated together. The resultant vector, pCGN7770, contains the pCGN7765 backbone with the napin seed specific expression cassette from pCGN3223.

The construct pCGN9873 contains the BrACX1 coding sequence in the antisense orientation under the control of the napin transcription initiation region and the *Cuphea pullcherrima* Fat B1 coding sequence under the control of the napin transcription initiation region.

The construct pCGN9874 contains the BrACX2 coding sequence in the antisense orientation under the control of the napin transcription initiation region and the *Cuphea pullcherrima* Fat B1 coding sequence under the control of the napin transcription initiation region.

The construct pCGN9875 contains the BrPKT2 coding sequence in the antisense orientation under the control of the napin transcription initiation region and the *Cuphea pullcherrima* Fat B1 coding sequence under the control of the napin transcription initiation region.

The construct pCGN9876 contains the AtACX1 coding sequence in the antisense orientation under the control of the napin transcription initiation region and the *Cuphea pullcherrima* Fat B1 coding sequence under the control of the napin transcription initiation region.

The construct pCGN9877 contains the BrACX2 coding sequence in the antisense orientation under the control of the napin transcription initiation region and the *Cuphea pullcherrima* Fat B1 coding sequence under the control of the napin transcription initiation region.

The construct pCGN9878 contains the AtPED1 coding sequence in the antisense orientation under the control of the napin transcription initiation region and the *Cuphea pullcherrima* Fat B1 coding sequence under the control of the napin transcription initiation region.

The construct pCGN9879 contains the AtPKT2 coding sequence in the antisense orientation under the control of the napin transcription initiation region and the *Cuphea pullicherrima* Fat B1 coding sequence under the control of the napin transcription initiation region.

The construct pCGN10413 contains the AtACX1 coding sequence in the sense orientation under the control of the napin transcription initiation region and the *Cuphea pullcherrima* Fat B1 coding sequence under the control of the napin transcription initiation region. The AtACX1 expression construct is oriented in the same direction of transcription as the Cpu Fat B1 expression construct.

The construct pCGN10414 contains the AtACX1 coding sequence in the sense orientation under the control of the napin transcription initiation region and the *Cuphea pullcherrima* Fat B1 coding sequence under the control of the napin transcription initiation region. The AtACX1 expression construct is oriented in the opposite direction of transcription from the Cpu Fat B1 expression construct.

The construct pCGN10416 contains the BrACX2 coding sequence in the sense orientation under the control of the napin transcription initiation region and the *Cuphea pullcherrima* Fat B1 coding sequence under the control of the napin transcription initiation region. The BrACX2 expression construct is oriented in the opposite direction of transcription from the Cpu Fat B1 expression construct.

The construct pCGN10417 contains the AtPED1 coding sequence in the sense orientation under the control of the napin transcription initiation region and the *Cuphea pullcherrima* Fat B1 coding sequence under the control of the napin transcription initiation region. The AtPED1 expression construct is oriented in the same direction of transcription as the Cpu Fat B1 expression construct.

The construct pCGN10419 contains the AtPKT2 coding sequence in the sense orientation under the control of the napin transcription initiation region and the *Cuphea pullcherrima* Fat B1 coding sequence under the control of the napin transcription initiation region. The AtPKT2 expression construct is oriented in the same direction of transcription as the Cpu Fat B1 expression construct.

The construct pCGN10421 contains the AtACX1-1 coding sequence in the sense orientation under the control of the napin transcription initiation region and the *Cuphea pullcherrima* Fat B1 coding sequence under the control of the napin transcription initiation region. The AtACX1-1 expression construct is oriented in the same direction of transcription as the Cpu Fat B1 expression construct.

The construct pCGN10423 contains the AtACX1-1 coding sequence in the antisense orientation under the control of the napin transcription initiation region and the *Cuphea pullcherrima* Fat B1 coding sequence under the control of the napin transcription initiation region. The AtACX1-1 expression construct is oriented in the opposite direction of transcription from the Cpu Fat B1 expression construct.

The construct pCGN10424 contains the AtPED1-1 coding sequence in the sense orientation under the control of the napin transcription initiation region and the *Cuphea pullcherrima* Fat B1 coding sequence under the control of the napin transcription initiation region. The AtPED1-1 expression construct is oriented in the same direction of transcription as the Cpu Fat B1 expression construct.

The construct pCGN10425 contains the AtPED1-1 coding sequence in the sense orientation under the control of the napin transcription initiation region and the *Cuphea pullcherrima* Fat B1 coding sequence under the control of the napin transcription initiation region. The AtPED1-1 expression construct is oriented in the opposite direction of transcription from the Cpu Fat B1 expression construct.

The construct pCGN10426 contains the AtPED1-1 coding sequence in the antisense orientation under the control of the napin transcription initiation region and the *Cuphea pullcherrima* Fat B1 coding sequence under the control of the napin transcription initiation region. The AtPED1-1 expression construct is oriented in the same direction of transcription as the Cpu Fat B1 expression construct.

The construct pCGN10417 contains the BrPED1 coding sequence in the antisense orientation under the control of the napin transcription initiation region and the *Cuphea pullcherrima* Fat B1 coding sequence under the control of the napin transcription initiation region. The BrPED1 expression construct is oriented in the same direction of transcription as the Cpu Fat B1 expression construct.

Example 5

Plant Transformation

A variety of methods have been developed to insert a DNA sequence of interest into the genome of a plant host to obtain the transcription or transcription and translation of the sequence to effect phenotypic changes.

The plant binary constructs described above are used in plant transformation to direct the expression of the ACOX and thiolase sequences from plant tissues.

Transgenic Brassica plants are obtained by Agrobacterium-mediated transformation as described by Radke et al. (*Theor. Appl. Genet.* (1988) 75:685–694; *Plant Cell Reports* (1992) 11:499–505). Transgenic Arabidopsis thaliana plants may be obtained by Agrobacterium-mediated transformation as described by Valverkens et al., (*Proc. Nat. Acad. Sci.* (1988) 85:5536–5540), or as described by Bent et al. ((1994), *Science* 265:1856–1860), or Bechtold et al. ((1993), *C.R.Acad.Sci, Life Sciences* 316:1194–1199). Other plant species may be similarly transformed using related techniques.

Alternatively, microprojectile bombardment methods, such as described by Klein et al. (*Bio/Technology* 10:286–291) may also be used to obtain nuclear transformed plants.

Example 7
Analysis of Transgenic Plants

Transgenic plants containing the expression constructs described above ACOX and thiolase sequences are analyzed for oil composition and content using techniques known in the art. Furthermore, seeds of transgenic plants are screened for germination rates.

The above results demonstrate that the nucleic acid sequences identified encode proteins which are involved in fatty acid β-oxidation. Such sequences find use in preparing expression constructs for plant transformations. The expression constructs provide a means for modifying the lipid content and composition in host plant cells, as well as for the inhibition or postponing of germination of seeds of plants containing constructs having such sequences.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claim.

What is claimed is:

1. An isolated DNA sequence having the sequence of SEQ ID NO: 7.

2. The isolated DNA sequence according to claim 1, wherein said nucleic acid sequence encodes acyl-CoA oxidase.

3. An isolated DNA sequence, wherein said nucleic acid sequence is complementary to a polynucleotide sequence having the sequence of SEQ ID NO: 7.

4. A nucleic acid construct comprising as operably linked components in the 5' to 3' direction of transcription:
   a transcriptional initiation region; and
   a polynucleotide sequence having the sequence of SEQ ID NO: 7.

5. A host cell comprising the nucleic acid construct of claim 4.

6. The host cell according to claim 5, wherein said host cell is selected from the group consisting of bacterial, insect, fungal, mammalian, and plant.

7. A plant comprising the host cell of claim 6.

8. A method for producing a recombinant host cell, comprising:
   transforming or transfecting a cell with a nucleic acid construct comprising as operably linked a transcriptional initiation region and a polynucleotide having the sequence of SEQ ID NO: 7 such that said host cell, under appropriate culture conditions, produces an protein encoded by said polynucleotide.

9. The method according to claim 8 wherein said host cell is a plant cell.

* * * * *